(12) United States Patent
Tabatadze et al.

(10) Patent No.: US 12,297,225 B2
(45) Date of Patent: May 13, 2025

(54) DETECTION METHOD FOR NATURAL AND MODIFIED SMALL NUCLEIC ACIDS

(71) Applicant: ZATA Pharmaceuticals, Inc, Worcester, MA (US)

(72) Inventors: David R. Tabatadze, Worcester, MA (US); Ivan B. Yanachkov, Shrewsbury, MA (US)

(73) Assignee: ZATA PHARMACEUTICALS, INC., Worcester, MA (US)

( * ) Notice: Subject to any disclaimer, the term of this patent is extended or adjusted under 35 U.S.C. 154(b) by 962 days.

(21) Appl. No.: 17/288,752

(22) PCT Filed: Oct. 25, 2019

(86) PCT No.: PCT/US2019/058078
§ 371 (c)(1),
(2) Date: Apr. 26, 2021

(87) PCT Pub. No.: WO2020/086970
PCT Pub. Date: Apr. 30, 2020

(65) Prior Publication Data
US 2021/0395292 A1  Dec. 23, 2021

Related U.S. Application Data

(60) Provisional application No. 62/750,952, filed on Oct. 26, 2018.

(51) Int. Cl.
*C07H 21/04* (2006.01)
*C12Q 1/6806* (2018.01)
*C12Q 1/6876* (2018.01)

(52) U.S. Cl.
CPC .......... *C07H 21/04* (2013.01); *C12Q 1/6806* (2013.01); *C12Q 1/6876* (2013.01)

(58) Field of Classification Search
CPC .... C07H 21/04; C12Q 1/6806; C12Q 1/6832; C12Q 1/6876; C12Q 2525/113; C12Q 2565/137

USPC ........................................................ 536/23.2
See application file for complete search history.

(56) References Cited

U.S. PATENT DOCUMENTS

| 2004/0063114 A1 | 4/2004 | Singh et al. |
| 2014/0220573 A1 | 8/2014 | Hrdlicka |
| 2017/0320902 A1 | 11/2017 | Tabatadze et al. |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*

* cited by examiner

*Primary Examiner* — Robert B Mondesi
*Assistant Examiner* — Mohammad Y Meah
(74) *Attorney, Agent, or Firm* — Fox Rothschild LLP

(57) ABSTRACT

The invention relates to a method for the detection of natural or modified nucleic acids by their sequence specific hybridization with charge-modified oligonucleotide probes having charge-modifying groups attached to their backbones. The charge-modifying groups partially or fully neutralize the net negative charge of the backbone of the oligonucleotide probes or render them with a net positive charge. The charge-modified oligonucleotide probes may or may not be labeled, for example, with fluorescent, visible or near-infrared dye, with radioactive or stable isotopes, or with high specific affinity binding groups. The charge-modified oligonucleotide probes facilitate the separation of their hybrids with the targeted nucleic acids from the unhybridized probes or from any other components of the analyzed sample. They also allow for the modification and optimization of the properties of the hybrids with the targeted nucleic acids, such as melting temperature, chromatographic properties and off-target specificity.

9 Claims, 14 Drawing Sheets

Specification includes a Sequence Listing.

SEQUENCE LISTING

<160> NUMBER OF SEQ ID NOS: 18

<210> SEQ ID NO 1
<211> LENGTH: 23
<212> TYPE: RNA
<213> ORGANISM: Artificial Sequence
<220> FEATURE:
<223> OTHER INFORMATION: RNA

<400> SEQUENCE: 1
uggacccuua gaaaguagua ucu                                          23

<210> SEQ ID NO 2
<211> LENGTH: 11
<212> TYPE: RNA
<213> ORGANISM: Artificial Sequence
<220> FEATURE:
<223> OTHER INFORMATION: 2'OMe Modification

<400> SEQUENCE: 2
auacuacuuu c                                                       11

```
<210> SEQ ID NO 3
<211> LENGTH: 11
<212> TYPE: RNA
<213> ORGANISM: Artificial Sequence
<220> FEATURE:
<223> OTHER INFORMATION: 2'OMe Modification

<400> SEQUENCE: 3
auacuacuuu c                                                          11

<210> SEQ ID NO 4
<211> LENGTH: 23
<212> TYPE: RNA
<213> ORGANISM: Artificial Sequence
<220> FEATURE:
<223> OTHER INFORMATION: RNA

<400> SEQUENCE: 4
uggacccuua gaaaggagua ucu                                             23

<210> SEQ ID NO 5
<211> LENGTH: 10
<212> TYPE: RNA
<213> ORGANISM: Artificial Sequence
<220> FEATURE:
<223> OTHER INFORMATION: 2'OMe Modification

<400> SEQUENCE: 5
auacuacuuu                                                            10

<210> SEQ ID NO 6
<211> LENGTH: 15
<212> TYPE: DNA
<213> ORGANISM: Artificial Sequence
<220> FEATURE:
<223> OTHER INFORMATION: DNA

<400> SEQUENCE: 6
tagaaagtag tatct                                                      15

<210> SEQ ID NO 7
<211> LENGTH: 23
<212> TYPE: RNA
<213> ORGANISM: Artificial Sequence
<220> FEATURE:
<223> OTHER INFORMATION: 2'OMe Modification

<400> SEQUENCE: 7
cacaaauucg guucuacagg gua                                             23

<210> SEQ ID NO 8
<211> LENGTH: 19
<212> TYPE: RNA
<213> ORGANISM: Artificial Sequence
<220> FEATURE:
<223> OTHER INFORMATION: 2'OMe Modification

<400> SEQUENCE: 8
agaguucugu ggaagucaa                                                  19

<210> SEQ ID NO 9
<211> LENGTH: 23
<212> TYPE: RNA
<213> ORGANISM: Artificial Sequence
<220> FEATURE:
```

```
<223> OTHER INFORMATION: RNA

<400> SEQUENCE: 9
uacccuguau aaccgaauuu gug                                    23

<210> SEQ ID NO 10
<211> LENGTH: 19
<212> TYPE: RNA
<213> ORGANISM: Artificial Sequence
<220> FEATURE:
<223> OTHER INFORMATION: 2'OMe and 2'F Modification

<400> SEQUENCE: 10
uugacuucca cagaacucu                                         19

<210> SEQ ID NO 11
<211> LENGTH: 11
<212> TYPE: RNA
<213> ORGANISM: Artificial Sequence
<220> FEATURE:
<223> OTHER INFORMATION: 2'OMe Modification

<400> SEQUENCE: 11
auacuacuuu c                                                 11

<210> SEQ ID NO 12
<211> LENGTH: 11
<212> TYPE: RNA
<213> ORGANISM: Artificial Sequence
<220> FEATURE:
<223> OTHER INFORMATION: 2'OMe Modification

<400> SEQUENCE: 12
auacuacuuu c                                                 11

<210> SEQ ID NO 13
<211> LENGTH: 16
<212> TYPE: RNA
<213> ORGANISM: Artificial Sequence
<220> FEATURE:
<223> OTHER INFORMATION: 2'OMe Modification

<400> SEQUENCE: 13
agaguucugu ggaagu                                            16

<210> SEQ ID NO 14
<211> LENGTH: 19
<212> TYPE: RNA
<213> ORGANISM: Artificial Sequence
<220> FEATURE:
<223> OTHER INFORMATION: 2'OMe Modification

<400> SEQUENCE: 14
uagacuucca cagaacucu                                         19

<210> SEQ ID NO 15
<211> LENGTH: 19
<212> TYPE: RNA
<213> ORGANISM: Artificial Sequence
<220> FEATURE:
<223> OTHER INFORMATION: 2'OMe Modification

<400> SEQUENCE: 15
agaguucugu ggaagucua                                         19
```

```
<210> SEQ ID NO 16
<211> LENGTH: 23
<212> TYPE: RNA
<213> ORGANISM: Artificial Sequence
<220> FEATURE:
<223> OTHER INFORMATION: RNA

<400> SEQUENCE: 16
uggacucuga gaaaggagua ugu                                               23

<210> SEQ ID NO 17
<211> LENGTH: 23
<212> TYPE: RNA
<213> ORGANISM: Artificial Sequence
<220> FEATURE:
<223> OTHER INFORMATION: 2'OMe Modification

<400> SEQUENCE: 17
acauacuccu uucucagagu cca                                               23

<210> SEQ ID NO 18
<211> LENGTH: 23
<212> TYPE: RNA
<213> ORGANISM: Artificial Sequence
<220> FEATURE:
<223> OTHER INFORMATION: 2'OMe Modification

<400> SEQUENCE: 18
acauacuccu uucucagagu cca                                               23
```

DETECTION METHOD FOR NATURAL AND MODIFIED SMALL NUCLEIC ACIDS

FIELD OF THE INVENTION

The present invention relates to a method for detection and/or quantification of natural or modified nucleic acids of interest using charge-modified oligonucleotide probes having charge-modifying groups which partially or fully neutralize the negative charge associated with the oligonucleotide backbone, or which provide slightly or highly positively charged oligonucleotides. The charge-modified oligonucleotide probes may be labeled with one or more reporter groups.

BACKGROUND

Naturally occurring short nucleic acids and, in particular, microRNAs are small non-coding RNAs that alter gene expressions and play a significant role in many disorders, including cancers. MicroRNAs have been recognized as new biomarkers for diagnosis, outcome prediction, and as therapeutic targets in cancer patients. Therefore, identification and quantification of the naturally occurring short nucleic acids in vivo or in vitro has clinical and medical value.

Additionally, therapeutic oligonucleotides (ONs) such as antisense ONs (ASO), small interfering RNAs (siRNA), antisense ON for exon-skipping, and aptamers or CRISPS technology associated small nucleic acids, such as gRNA and single stranded or double stranded template (gene editing) DNAs are some of the most promising drug candidates for treatment of cancers, infectious diseases, genetic diseases, and a host of other morbidities where gene expression modulation or gene editing could be beneficial. Therefore, identification and quantification of these ONs of interests in vivo or in vitro has clinical and medical value.

The scientific literature contains a number of methods for detecting small nucleic acids of natural occurrence or in result of treatment using hybridization with complementary ONs.

WO1996/006189 discloses qualitative and quantitative detection of ONs, in which complementary peptide nucleic acid (PNA) oligomers connected to detectable labels are hybridized to the target ONs and the hybrids are analyzed by CE and appropriate detector.

Raynaud et al. disclose in the Journal of Pharmacology and Experimental Therapeutics, vol. 281, pages 420-427 (1997) a method for quantitative detection of ONs after hybridization with complementary PNA probe labeled with fluorescent dye, followed by HPLC analysis using fluorescence detector. A similar method, based on PNA hybridization assay has been described by Godinho et al. in Journal of Nucleic Acid Therapeutics, vol. 27, pages 323-34 (2017).

WO2010/043512 discloses the use of a fluorescently labelled PNA ON probe for detection and quantification of oligonucleotides after hybridization, ion-exchange HPLC separation of the formed duplexes from the probe excess, and detection/quantification by fluorescent detector.

Each of these methods have disadvantages associated with the use of PNA-based detection probes, particularly, insufficient aqueous solubility of the peptide nucleic acids probes, tendency of their solutions to aggregate and precipitate over time, high cost, the possibility of false detection by hybridization to partially mismatched sequences, and the inability to control and modify the retention time of the hybrids.

WO2008/046645 discloses the use of locked nucleic acid (LNA) probes in a real time polymerase chain reaction, RT-PCR-based ON detection assay. The disadvantages of the use of RT-PCR methods for analysis of short nucleic acids include low specificity and accuracy due to the use of very short primers. In addition, the use of LNA based probes introduces the possibility of false detection due to hybridization with partially mismatched sequences.

WO2017/068087 discloses a method for the detection of ONs of interest using fluorescently labelled LNA ON probes and anion exchange high performance liquid chromatography coupled with fluorescence detection to analyze and quantify the duplexes of the probes with the ONs of interest. This method, similarly to the method disclosed in WO2008/046645 has disadvantages associated with the use of LNA probes—false positive detection by hybridization with partially mismatched ON sequences due to the very high melting temperature of the LNA duplexes and the inability to modify and adjust the retention time of the duplexes by modifying their total negative charge.

There is a need in the art for additional and improved probes for use in the detection and/or quantification of nucleotides of interest. The invention provided herein addresses the problems discussed above as well as others, as will be apparent from the following disclosure.

SUMMARY OF THE INVENTION

The present invention provides a highly sensitive and versatile method for identification and/or quantification of one or more natural or modified nucleic acids in a sample. The sample may include, without being limited to an organism, including a microorganism, tissue, blood, plasma, urine or other biological fluid, cell culture and ON based Active Pharmaceutical Ingredient (API) of drug formulations.

The invention provides a method for the detection of natural or modified nucleic acids of interest by their sequence specific hybridization with charge-modified oligonucleotide probes (referred to herein as "Z-probes"), which have charge-modifying groups attached to their backbones. The charge-modifying groups partially or fully neutralize the net negative charge of the oligonucleotide backbone or render the Z-probes net-positively charged. The Z-probes may or may not be labeled with a detectable reporter group, for example a fluorescent, visible or near-infrared dye, a radioactive or stable isotope, or a high specific affinity binding group.

The duplexes formed between the target nucleic acids and the Z-probes may be analyzed by anion exchange high performance liquid chromatography, gel-electrophoresis, or anion exchange solid phase cartridge, or by any other chromatographic or charge separation-based modality or high affinity binding, and detected and quantified by fluorescence, ultraviolet, visible or near-infrared light spectroscopy, radioactivity detection or mass-spectrometry.

The invention also relates to the use of such a detection method for quantifying cellular uptake, metabolism and tissue distribution of an ON of interest when administered in-vivo, artificially expressed, or presented in a sample.

The invention also relates to the use of such a detection method for the identification, quantification, and distribution study of naturally occurring or artificially expressed small nucleic acids of interest including but not limited to microRNA, mRNA, tRNA, snRNA, piRNA, pathogen DNA or RNA, or synthetic ONs, including but not limited to oligotherapeutics, antisense ON, siRNA or aptamers, in-vivo or in a sample.

DETAILED DESCRIPTION OF THE INVENTION

Definitions

Small Nucleic Acid

Figure 1:
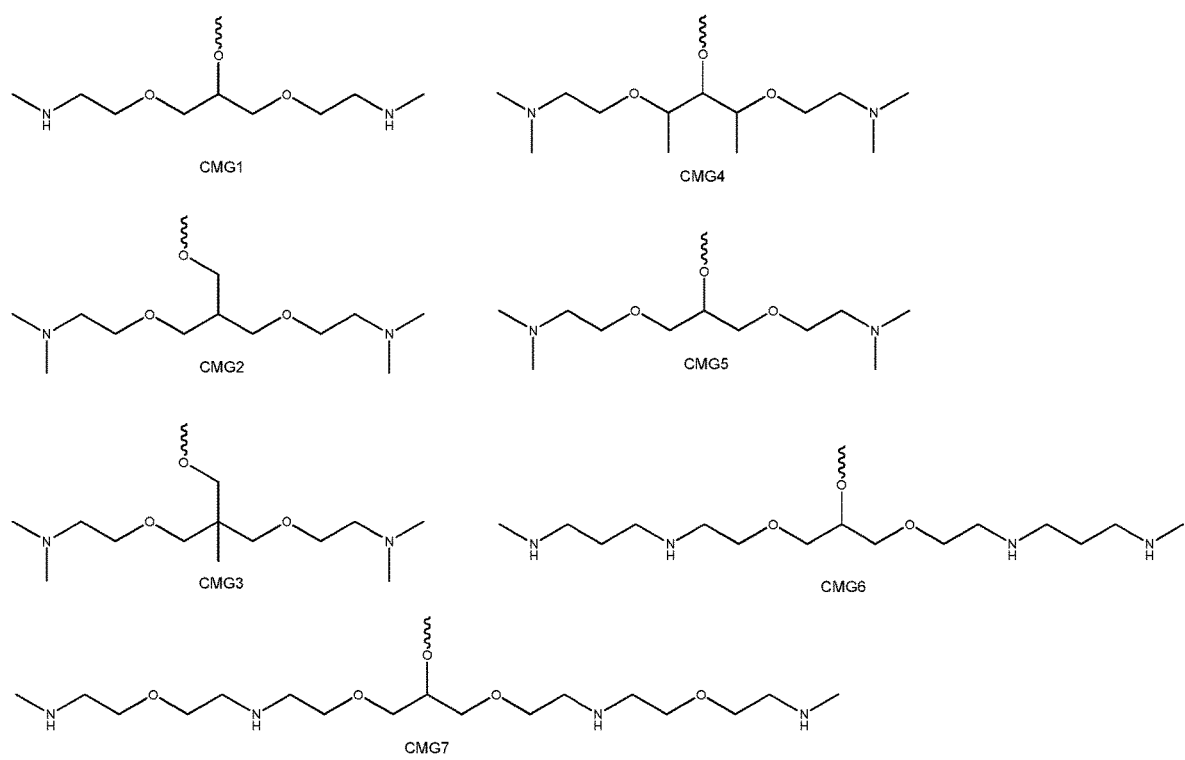
FIG. 1 illustrates some representative examples of charge-modifying groups (CMGs). The wavy line (∼∼∼) represents the point of attachment of the CMG to the oligonucleotide portion of the Z-probe, which may optionally be through a spacer group (not shown)

In embodiments of the invention the target nucleic acid may be a small nucleic acid. The term "small nucleic acid" as used herein is defined as a synthetic or naturally occurring molecule comprised of two or more and up to two thousand covalently linked nucleosides or modified nucleosides or nucleoside analogs or nucleoside mimics through a phosphate group, or phosphate group analog or phosphate group mimic or through any other divalent chemical moiety. The terms "small nucleic acids" also encompasses the duplexes or aggregates formed by H-bonding, base pairing, and in particular, Watson-Crick type base pairing between two or more single-stranded small nucleic acids. In this context, small refers to nucleic acids that comprise from 6 to 2000 nucleotides in length, or from 10 to 1000 nucleotides in length, or from 10 to 500 nucleotides in length, or from 10 to 100 nucleotides in length.

Such small nucleic acids may also be referred to as DNA, RNA, DNA oligonucleotides, RNA oligonucleotides, oligonucleotides, ON, ONs, natural or synthetic ONs or modified ONs. Modified ONs may be, without being limited to, peptide nucleic acids (PNA), morpholino oligonucleotides (PMO), locked nucleic acids (LNA), bridged nucleic acids (BNA), bicyclic-(BC), or tricyclic (TC) nucleic acids. The modified ONs can also include ONs containing simultaneously different types of modifications, i.e. being chimeric in nature, and can contain monomers (nucleosides or nucleoside equivalents or nucleoside mimics) of different types. Small nucleic acids can include any type of modified oligonucleotides or oligonucleotide analogs of up to 2000 monomers, regardless of their chemistry or composition.

Such small nucleic acids can encompass different types of natural or synthetic nucleic acids regardless of their function, place of occurrence, use or intended use, such as single, or double stranded RNA, microRNA (miRNA, miR, both mature or pre-miRNA and their guide and passenger strands), transport RNA (tRNA) messenger RNA (mRNA), piwi-interacting RNA (piRNA), pathogens generated DNA or RNA, such as viral RNA or DNA, small interfering RNA (siRNA) or any of its strands, guiding RNA (gRNA), tracer RNA, single or double stranded DNA enabling editing of genes (in CRISPR/Cas9).

Such small nucleic acids also encompass the product of conjugation, covalent or non-covalent bonding of any small nucleic acid with any chemical moiety, regardless of the type of the chemical moiety and the purpose of this conjugation, which may be intended, without being limited to, targeting, packing, modifying of the biological, chemical, physical-chemical properties, stability, or solubility.

Such small nucleic acids of interest may also include the in vivo or in vitro metabolites of small nucleic acids, or the products of their splicing or any other naturally occurring in vivo or in vitro processing or modification.

Oligonucleotide

The term "oligonucleotide" (ON) as used herein in some embodiments is defined as nucleic acids formed through in vivo or in vitro process or made by chemical synthesis, or by combination of those. In some embodiments, the oligonucleotide may be a probe, which optionally contains reporter modalities, and is commonly made by chemical synthesis followed by purification.

Probe

The term "probe" as used herein is defined as an oligonucleotide, which may or may not contain a reporter group or a detectable isotope attached to it, and which oligonucleotide can be used for detection, analysis and/or quantification of target nucleic acids in a sample by the sequence specific hybridization of the probe to the target nucleic acid(s).

Z-Probe

The term "Z-probe" or "charge-modified oligonucleotide probe" as used herein refers to a synthetic oligonucleotide probe which has one or more charge-modifying groups (CMG) covalently attached to its backbone, and which charge-modified oligonucleotide can be used for detection, analysis and/or quantification of target nucleic acids in a sample.

The Z-probe may or may not have one or more reporter groups covalently attached to it. Reporter group(s) may be covalently attached on the internucleotide linkages or their equivalents and/or to the termini of Z-probe and/or to the nucleoside sugars or their equivalents or to the nucleoside bases or their equivalents, optionally through a linking moiety. It will also be understood that Z-probe can comprise any modified or non-modified ON, nucleosides, and any modified or non-modified internucleotide/internucleoside linkages, and any combination of those in its molecule. It will also be understood that the CMG and the reporter groups can be linked to the Z-probe directly or via spacers, or through other chemical moieties.

Spacer/Linker

A "spacer" or "linker" is a divalent group, which may be a single atom, or a chemical group (linear, branched or cyclic) which is covalently connected to two chemical moieties. Linker groups may be optionally used to covalently link a CMG to the backbone of the oligonucleotide of a Z-probe. Alternatively, or additionally, a linker group may optionally be used to covalently link one or more reporter groups to the Z-probe. Examples of linkers include divalent atoms such as —O— or —S—; linearly connected carbon atoms such as alkylenes, and particularly $C_{1-10}$ alkylenes (i.e., alkane-1,Ω-diyls), such as —$CH_2$—, —$CH_2CH_2$—, —$CH_2CH_2CH_2$—, —$CH_2CH_2(CH_3)CH_2$—, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, such as —$OCH_2$—, —$CH_2OCH_2$—, and —O—$(CH_2CH_2O)_x$—, wherein x is 1 to 10, such as —$OCH_2CH_2O$—, —$OCH_2CH_2OCH_2CH_2O$— and —$OCH_2CH_2OCH_2CH_2OCH_2CH_2O$—, divalent ring systems such as cis and trans cyclopropylene and cyclohexan-1,4-diyl; and the like. Particular linkers may be selected from an oxygen atom, sulfur atom, methylene group, substituted methylene group, ethylene group, and substituted ethylene group.

Reporter

The term "reporter" or "reporter moiety" or "reporter group" as used herein is referring to a chemical moiety or moieties or atom or a group of atoms, which possesses detectable properties, including but not limited to spectroscopic properties (i.e. absorption or emission of visible, ultraviolet, or infrared light) or radioactive properties (emission of different detectable particles or high energy photons) or specific molecular weight or isotopic pattern, or nuclear or electronic spin properties. The reporter group can also be a chemical moiety that can bind, covalently or non-covalently to another group, moiety or molecule, which can then be used for detection purposes. An example of such a group is biotin, which can be used for avidin-based detection assay, or any antigen, which can be used for ELISA based assay. It is understood that one skilled in the art can envision different types detectable properties or features that can be used for many different methods of detection or assays, which are also a part of this definition.

Backbone

"Backbone" refers to the repetitive sugar-phosphate moieties occurring in the DNA, RNA, or modified sugar or modified phosphate, or sugar-phosphate equivalents, or sugar and/or phosphate mimics occurring in the modified oligonucleotides. The phosphate moieties or phosphate moiety equivalents in some embodiments can also be addressed as linkage or internucleoside/internucleotide linkage.

Charge Modifying Groups (CMGs)

"Charge-modifying groups" (CMGs) or "charge neutralizing groups" or "backbone charge modifying group", or "charge modifying moiety" refers to branched symmetrical and non-symmetrical chemical moieties which contain positively charged atoms (such as N at physiological/neutral pH) and are linked directly or through a spacer to the internucleoside phosphate, or phosphate equivalent, of the Z-probes. In some cases, a CMG group can be linked to the phosphate or phosphate equivalent located at the termini of the Z-probe. CMG comprises two or more positive charges (at least at neutral pH) that can neutralize or modify the local or the overall charge of the Z-probe, or hybrid when associated with a target nucleic acid. Examples of CMG groups are provided in FIG. 1. The charge-modifying group may be depicted herein in its neutral form, however it is understood that during use, one or more of the nitrogens in the charge-modifying group will be protonated and accordingly have a positive charge. In some embodiments, particularly at physiological pH or at lower pH, each of the nitrogens in the charge-modifying group may be protonated.

Sample

The term "sample" as used herein is defined as a composition, organism, prokaryotes, eukaryotes, or in vivo or ex vivo system that also include tissue, blood, plasma, urine, or any other biological fluid, biopsy, cell culture, ON-based drug formulation, active pharmaceutical ingredients (API), or any other substance or media or body that can contain the nucleic acids of interest (i.e., the target nucleic acid).

Small Nucleic Acid Metabolite or ON Metabolite

The term "small nucleic acid metabolite" or "ON metabolite" includes natural or modified small nucleic acids or ONs or their conjugates from which one or more nucleotides are deleted from the termini, or which have been cleaved by nucleases or hydrolyzed by any other mechanism, or in which one or more nucleobases have been removed or modified, or which have been chemically modified though biological or spontaneous chemical process in vivo, ex vivo or in vitro.

Oligotherapeutics

The term "oligotherapeutics" as used herein is defined as synthetic oligonucleotide(s), or their derivatives, or their conjugates with other chemical moieties, or the constructs of their aggregations with other modalities in all combinations, or artificially made gene construct or vector, that can elicit or is presumed to elicit desirable biological effect. The term oligotherapeutics fully or partially applies to one of the oligotherapy approaches, known in the field as antisense, CRISPR, exon-skipping, RNA interference, aptamer, microRNA, or siRNA approaches. The oligotherapeutics of interest may be an antisense oligonucleotide, siRNA, aptamer, gRNA or split gRNA, template single or double stranded DNA enabling editing of genes, or spiegelmers or a mixture of such oligonucleotides.

Internucleoside Linkage

The term "internucleoside linkage" is defined as a phosphodiester linkage, that covalently connects two nucleosides together in the natural nucleic acids, or as a modified phosphodiester that connects two monomers in the modified ONs, or as a phosphate mimic or equivalent that couples together the nucleoside equivalents in some modified ONs, such as PNA or PMA.

Base or Nucleobase

The term "base" or "nucleobase" or "nucleoside base" as used herein is a chemical moiety that is covalently attached to the ribose sugar moiety (sugar equivalent, or sugar mimic) of the backbone of the ONs and can be involved in a sequence-specific hydrogen bonding with other natural or non-natural bases of nucleic acids or modified nucleic acids. The base can be natural type (uracil, thymine, cytosine, adenine, guanine), modified natural nucleobase (5-hydroxyethyluracil, 5-fluorouracil, 7-deazapurines) or other chemical structure that can be involved in specific Watson-Crick or non-Watson-Crick type of base pairing.

Sugar Moiety

The term "sugar" or "nucleoside sugar" or "ribose sugar" as used herein refers to a naturally-occurring ribose sugar moiety (i.e., found in DNA or RNA) or modified ribose sugar moiety or ribose sugar moiety equivalent, or other trivalent chemical group. Natural nucleoside sugars are ribose or 2'-deoxyribose. Modified ribose sugars include, for example, those existing in LNA, BNA, tricyclo-DNA (tc-DNA), 2'-O-alkyl-RNAs, such as 2'-O-methyl-RNA, 2'-alkoxy-RNAs, 2'-O-methoxyethyl-RNA (MOE), 2'-amino-DNA, 2'-fluoro-RNA, arabino-ONs. The sugar moieties may be selected from, for example, D-ribose, D-2'-deoxyribose, 2'-O-substituted ribose, L-ribose, L-deoxyribose, D- or L-arabinose, D- or L-lyxose, α- or β-D-furanose, α- or β-L-furanose, 2'-O-substituted-α- or β-D-furanose, 2'-4'-bridged-β-D-furanose, 3'-5'-tricyclo-2'-deoxy-D-ribose (tc-deoxyribose).

The present invention relates to a method for detection and/or quantification of natural or modified small nucleic acid(s) of interest using Z-probes, which are synthetic ONs having one or more charge-modifying groups, referred as CMGs, wherein the CMGs are covalently attached to the internucleoside linkages of the Z-probe. The CMGs neutralize, or modify the local, or net charge of the Z-probe or it hybrid when hybridized to a nucleic acid of interest. Depending on the number and type of the CMGs, the Z-probe may have partial, or zero net negative charge, or may have low, or high net positive charge. The Z-probe may or may not be connected to one or more reporter groups, or to one or more chemical moieties with high specific affinity to certain ligands. The Z-probe has a sequence, or contains such a sequence, that is complementary to the target nucleic acid(s) or to a region of the target nucleic acid(s), or to one strand of a duplex or triplex nucleic acid(s) of interest.

When the Z-probe makes contact with a sample containing the target nucleic acid of interest, it forms a duplex with the target nucleic acid, and the duplex can then be separated from any excess of Z-probe, and from any other component of the sample by using, but without being limited to, ion-exchange HPLC, or electrophoresis, or capillary electrophoresis (CE), or by reversed-phase HPLC especially reversed phase HPLC utilizing ion-pairing modifier or by affinity biding or chromatography. It is also understood that if the Z-probe is conjugated to a high specificity affinity moiety, such as biotin, this moiety can be used for separation of the duplex of the Z-probe from any other sample components, and for its detection and quantification.

By varying the type, number and the position of the CMGs attached to the Z-probe, the stability of its duplex with the target nucleic acid may be optimized, and the possibility of forming stable duplexes with partially mismatched nucleic acids may be minimized. Also, by optimizing the type, the number and the position of the CMGs attached to the Z-probe, the separation of the Z-probe duplex with the target nucleic acid from the excess of (unpaired) Z-probe and from other components of the sample can be facilitated.

The reporter group that may be optionally attached to the Z-probe may provide for specific and sensitive methods of detection and quantification of the Z-probe duplex. In some embodiments, the detection and quantification of the Z-probe duplex can be achieved without the use of a detection probe. Instead, the Z-probe duplex with the target nucleic acid may be detected and quantified using universal detection methods, such as UV absorption, or mass-spectrometry.

In some embodiments, the Z-Probes have the structure (I):

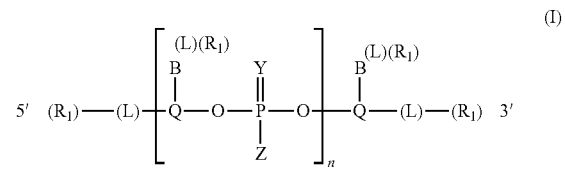

wherein:
    each B is a nucleoside base independently selected from A, G, C, T, U or other nucleobase moiety, modified nucleobase moiety, nucleobase moiety equivalent, nucleobase moiety mimic or other moiety that can take part in sequence specific base-pairing;

each Q is independently selected from a nucleoside sugar, including naturally-occurring ribose sugar moieties (i.e., found in DNA or RNA) or modified ribose sugar moieties or ribose sugar moiety equivalent, or other trivalent chemical group;

wherein, when Q is natural or modified ribose, B is connected to the 1' carbon atom of Q and the oxygen atoms of the phosphate or the substituted phosphate groups are connected to the 3' and 5' carbon atoms, respectively;

each Y is independently selected from a sulfur or oxygen atom;

n is a number from 1 to 250, and preferably from 8 to 150;

each L is, independently for each occurrence, a

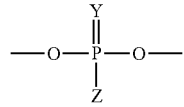

group, or a linker selected from divalent atoms such as —O— or —S—; linearly connected carbon atoms such as alkylenes, and particularly $C_{1-10}$ alkylenes, such as —$CH_2$—, —$CH_2CH_2$—, —$CH_2CH_2CH_2$—, —$CH_2CH_2(CH_3)CH_2$—, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, such as —$OCH_2$—, —$CH_2OCH_2$—, and —O—$(CH_2CH_2O)_x$—, wherein x is 1 to 10, such as —$OCH_2CH_2$—, —$OCH_2CH_2OCH_2CH_2O$— and —$OCH_2CH_2OCH_2CH_2OCH_2CH_2O$—, divalent ring systems such as cis and trans cyclopropylene and cyclohexan-1,4-diyl; or L is not present, in which case L is a covalent bond;

each $R_1$ is, independently for each occurrence, a reporter group, or a group with high specific affinity, or a hydrogen atom;

each Z is independently selected from the group consisting of OH, SH, or a group with Structure (II)

—, wherein x is 1 to 10, such as —$OCH_2CH_2O$—, —$OCH_2CH_2OCH_2CH_2O$— and —$OCH_2CH_2OCH_2CH_2OCH_2CH_2O$—, divalent ring systems such as cis and trans cyclopropylene and cyclohexan-1,4-diyl; or W is not present, in which case W is a covalent bond;

each X is independently selected to be an oxygen or a sulfur atom;

each $R_2$ is independently selected from a group consisting of H, methyl, ethyl, propyl, isopropyl, methoxy, ethoxy, isopropyloxy, straight, branched, or substituted $C_{1-6}$ alkyl, $C_{2-6}$ alkene, substituted $C_{2-6}$ alkene, straight or branched $C_{1-6}$ alkoxy, or two $R_2$ together with the nitrogen atom to which they are attached form an 5- to 7-membered single nitrogen heterocyclic ring, or 5- to 7-member heterocyclic ring having up to two additional ring heteroatoms selected from the group consisting of O, S, and N, and wherein the 5- to 7-membered heterocyclic ring may be unsubstituted or substituted with up to three substituents selected from the group consisting of halo, $C_{1-4}$ alkyl, and $C_{1-4}$ alkoxy, or is not present, in which case $R_2$ is an electron pair;

$R_3$ is selected from a group consisting of H, methyl, ethyl, propyl, isopropyl, 1,1-dimethyethyl, methoxy, ethoxy, isopropyloxy, tret-butyloxy, $C_{1-6}$ straight or branched alkyl, substituted $C_{1-6}$ straight or branched alkyl, $C_{2-6}$ alkene, and substituted $C_{2-6}$ alkene;

each $R_4$ is independently selected from a group consisting of H, methyl, ethyl, propyl, isopropyl, methoxy, ethoxy, isopropyloxy, straight, branched, or substituted $C_{1-6}$ (II)

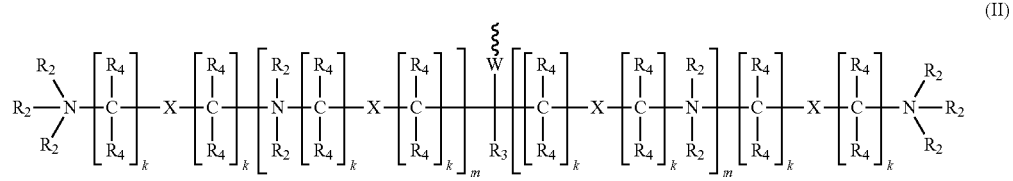

wherein:
at least one occurrence of Z is selected to be a group according to Structure II;
W is a linker selected from divalent atoms such as —O— or —S—; linearly connected carbon atoms such as alkylenes, and particularly $C_{1-10}$ alkylenes, such as —$CH_2$—, —$CH_2CH_2$—, —$CH_2CH_2CH_2$—, —$CH_2CH_2(CH_3)CH_2$—, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, such as —$OCH_2$—, —$CH_2OCH_2$—, and —O—$(CH_2CH_2O)_x$ alkyl, $C_{2-6}$ alkene, substituted $C_{2-6}$ alkene, straight or branched $C_{1-6}$ alkoxy, or two $R_4$ together with the carbon atom to which they are attached form an 3- to 7-membered alicyclic ring, or 5- to 7-member heterocyclic ring having up to two ring heteroatoms selected from the group consisting of O, S, and N, and wherein the alicyclic or heterocyclic ring may be unsubstituted or substituted with up to three substituents selected from the group consisting of halo, $C_{1-4}$ alkyl, and $C_{1-4}$ alkoxy;

each k is independently, for each occurrence selected from 2, 3, 4 or 5; and each m is independently, or each occurrence selected from 0, 1, 2, 3, 4 or 5.

The group with Structure (II) may be selected to be a group having the Structure IIA:

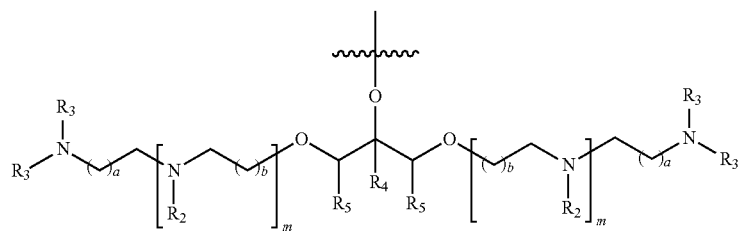

IIA wherein:
  each $R_2$ is independently selected from the group consisting of H, $C_{1-6}$ alkyl, substituted $C_{1-6}$ alkyl, $C_{2-6}$ alkene, and substituted $C_{2-6}$ alkene;
  each $R_3$ is independently selected from the group consisting of H, $C_{1-6}$ alkyl, substituted $C_{1-6}$ alkyl, $C_{2-6}$ alkene, and substituted $C_{2-6}$ alkene;
  alternatively, two adjacent $R_3$, together with the nitrogen to which they are attached, form a 5- to 7-membered heterocyclic ring having up to two additional ring heteroatoms selected from the group consisting of O, S, and N, and wherein the 5- to 7-membered heterocyclic ring may be unsubstituted or substituted with up to three substituents selected from the group consisting of halo, alkyl, $C_{1-4}$ alkyl, and $C_{1-4}$ alkoxy;
  $R_4$ is selected from the group consisting of H, $C_{1-6}$ alkyl, substituted $C_{1-6}$ alkyl;
  each $R_5$ is independently selected from the group consisting of H, $C_{1-6}$ alkyl (such as methyl, ethyl, propyl, iso-propyl) or substituted $C_{1-6}$ alkyl;
  each a is independently selected from 1, 2, 3 or 4;
  each b is independently selected from 1, 2, 3; or 4 and
  each m is independently selected from 0, 1, 2, 3, or 4.

In some embodiments, Z-Probes have the structure (IA):

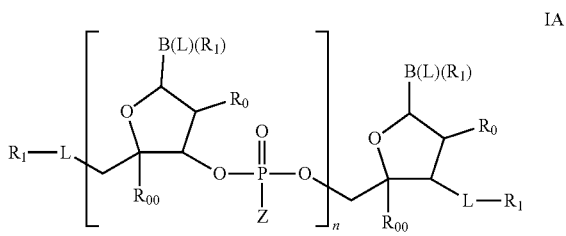

IA wherein:
  each B is in a nucleoside base, independently selected from A, G, C, T, U or other nucleobase moiety, modified nucleobase moiety, nucleobase moiety equivalent, nucleobase moiety mimic or any moiety that can take part in sequence specific base-pairing;
  n is a number from 1 to 250, and preferably from 8 to 150;
  L is independently, for each occurrence, a

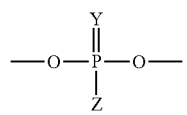

group, a linker selected from divalent atoms such as —O— or —S—; linearly connected carbon atoms such as alkylenes, and particularly $C_{1-10}$ alkylenes, such as —$CH_2$—, —$CH_2CH_2$—, —$CH_2CH_2CH_2$—, —$CH_2CH_2(CH_3)CH_2$—, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, such as —$OCH_2$—, —$CH_2OCH_2$—, and —O—$(CH_2CH_2O)_x$—, wherein x is 1 to 10, such as —$OCH_2CH_2$—, —$OCH_2CH_2OCH_2CH_2O$— and —$OCH_2CH_2OCH_2CH_2OCH_2CH_2O$—, divalent ring systems such as cis and trans cyclopropylene and cyclohexan-1,4-diyl; or is not present, in which case L is a covalent bond;
  each $R_0$ is independently selected from H, OH, or O—$C_{1-3}$ alkyl, substituted O—$C_{1-3}$ alkyl, O—$CH_2CH_2OCH_3$, F, or together with $R_{00}$ is a divalent moiety that forms a bridge between C2' and C4' such as —$OCH_2$—, or —$OCH_2CH_2$—;
  each $R_{00}$ is either, together with $R_0$ a divalent moiety that forms a bridge between C2' and C4' such as —$OCH_2$—, or $OCH_2CH_2$—, or is a H;
  each $R_1$ is independently selected from a reporter group, or a group with high specific affinity, or a hydrogen atom;
  each Z is independently selected from the group consisting of OH, SH, or a group with Structure II or Structure IIA, optionally connected through a linker, wherein at least one Z is selected to be a group with Structure II or IIA.

The term "alkyl" refers to the radical of saturated aliphatic groups, including straight-chain alkyl groups and branched-chain alkyl groups. Unless the number of carbon atoms is otherwise specified, alkyl as used herein means an alkyl group, as defined above, but having from one to six carbon atoms, and more preferably from one to four carbon atoms. The term "lower alkyl" refers to alkyl groups having 1 to 3 carbon atoms. Alkyl groups include methyl, ethyl, propyl, isopropyl, n-butyl, iso-butyl, tert-butyl, cyclopropyl and cyclobutyl.

The term "substituted alkyl" refers to an alkyl group as defined above and, in addition, having one to three substituents. The substituents are selected from the group consisting of halo, hydroxy, lower alkoxy, amino, lower alkyl amino, nitro, cyano, perfluoro alkyl, and perfluoro alkoxy.

The term "alkene" refers to the radical of unsaturated aliphatic groups, including straight-chain alkene groups and branched-chain alkene groups. Unless the number of carbons is otherwise specified, alkene groups have from two to six carbons, and more preferably from two to four carbon atoms. The term "substituted alkene" refers to an alkene group as defined above and having, in addition, one to three substituents. The substituents are selected from the group consisting of halo, hydroxy, lower alkoxy, amino, lower alkyl amino, nitro, cyano, perfluoro alkyl, and perfluoro alkoxy.

As used herein, the definition of each expression, e.g. alkyl, m, n, $R_1$, $R_2$, $X_1$, $X_2$ etc., when it occurs more than once in any structure, is intended to be independent of its definition elsewhere in the same structure.

In some embodiments of structure (I) the reporter group $R_1$ can be the same or different reporter moiety such as a fluorescent dye, or a fluorescent dye which is sensitive to its environment and especially to the state and degree of hybridization of the structure (I) with complementary ONs, or a fluorescent quencher, a dye that absorbs light in the visible, or near-visible infrared or ultraviolet specter, or chemical moiety that contains one or more radioactive isotopes, such as, $^{31}P$, $^{14}c$, or $^{3}H$, $^{35}S$, $^{131}I$, $^{111}In$ or, $^{99m}Tc$, or one or more stable isotopes, such as $^{2}H$, $^{18}O$, $^{13}C$, $^{15}N$, or a moiety with high specific affinity binding to another moiety, such as biotin, which has high specific affinity to avidin, or an antigen with a high specific binding to an antibody.

The chemical moiety having structure (II) can be introduced in the Z-probes by employing, at least in part, the phosphoroamidites and the methods disclosed in WO2016/081600A1 and by Yanachkov et al. in "Self-neutralizing oligonucleotides with enhanced cellular uptake", Org. Biomol. Chem., vol. 15 (6), pages 1363-80 (2017), which are hereby incorporated in their entirety by reference.

The nucleoside base moieties of the Z-probes may contain natural bases, such as T, U, C, G and A, or may contain a different number, combination and sequence of non-natural bases, such as C5 substituted pyrimidines (e.g. C5-halogen, C5-ethyne, C5-propyne and C5-thiazole U and C), 2-thio-U and 2-thio-T, diaminopurine, 7-deazapurines and $N^2$-substituted guanine. Many different oligonucleotides with modified nucleobases are known to one skilled in the art and can be used as part of the Z-probes. A large number of base modified ONs have been described by W. B. Wan and Seth P. P. in the *Journal of Medicinal Chemistry*, vol. 59, pages 9645-9667 (2016) and in the references provided therein and are each incorporated herein by reference. Introduction of different nucleobase modifications can be used to modulate and tune the strength and specificity of the base pairing properties of the Z-probes with the target nucleic acids.

The sugar moieties of the Z-probes (groups Q in structure I) may be of only one type or may be of more than one type and in various numbers, sequences and arrangements. For instance Z-probes may contain natural nucleoside sugars (Q is ribose or 2'-deoxyribose), or may contain modified sugars, for example, such as those existing in LNA, BNA, tricyclo-DNA (tc-DNA), 2'-O-alkyl-RNAs, such as 2'-O-methyl-RNA, 2'-alkoxy-RNAs, 2'-O-methoxyethyl-RNA (MOE), 2'-amino-DNA, 2'-fluoro-RNA, arabino-ONs, or others in all combinations. The sugar moieties may be selected from D-ribose, D-2'-deoxyribose, 2'-O-substituted ribose, L-ribose, L-deoxyribose, D- or L-arabinose, D- or L-lyxose, α- or β-D-furanose, α- or β-L-furanose, 2'-O-substituted-α- or β-D-furanose, 2'-4'-bridged-β-D-furanose, 3'-5'-tricyclo-2'-deoxy-D-ribose (tc-deoxyribose). Many different sugar modified oligonucleotides are known to one skilled in the art and can be applied as part of the Z-probes. A large number of sugar modified ONs have been described by W. B. Wan and Seth P. P. in the *Journal of Medicinal Chemistry*, vol. 59, pages 9645-9667 (2016) and in the references described therein and are incorporated herein by reference. Introducing modified sugars in the Z-probes can significantly enhance their resistance to enzymatic degradation and their in vivo stability and can have significant effect on the strength of their base-pairing with complementary small nucleic acids and can be used to modulate and tune those properties.

The internucleoside linkage of the Z-probes can be of phosphotriester type (Y being an oxygen in structure 1) or it may be of thiophosphonate type (Y being a sulfur structure I), or it can be of various combinations and sequences of those. Introduction of thiophosphonate internucleoside linkages in the Z-probes may increase their stability toward enzymatic degradation and their in vivo stability and lowers the stability of the corresponding duplexes and can be used to modulate and tune those properties.

The reporter groups of the Z-probes can be attached to the Z-probes 3'-end, 5'-end, to the nucleobases, or to the internucleoside linkages (i.e., internucleoside phosphate groups). The attachment of different fluorescent labels or other groups through a diphosphate ester to the 5' or the 3' termini can be accomplished using commercially available phosphoroamidites and/or control pore glasses during the automated synthesis.

The reporter groups can be attached to the nucleobases of the ONs, preferably to the C5 of the pyrimidines and C8 of the purine bases, by using amino-group functionalized nucleobases which can be coupled post-synthetically with amino-group reactive dyes or affinity groups, or ethynyl group functionalized bases which can be coupled post-synthetically with azide-group functionalized dyes or affinity groups by using Click chemistry.

The reporter groups can be attached to the internucleoside linkages as disclosed by Tabatadze et al. in U.S. Pat. No. 8,084,589 and in Nucleosides Nucleotides Nucleic Acids, vol. 27 (2), pages 157-172 (2008), and by Zang et al. in Proc. Natl. Acad. Sci. USA, vol. 105 (11), pages 4156-61 (2008) which are incorporated in their entirety herein by reference.

If the reporter groups are radioactive or stable isotopes, they can be incorporated during the automated synthesis using labeled phosphoramidites, or during the oxidative step using labeled oxidation or sufurization agents, or post-synthetically, by exchange, using for instance, tritiated or deuterated water.

Detection and quantification of target nucleic acids, and particularly small nucleic acids, have clinical and medical value for research, detection, diagnosis, prognosis and treatment of various disorders including but not limited to cancer, genetic disorders, metabolic disorders, immune disorders, infectious diseases and orphan diseases.

The Z-probes of the present invention can be used to detect the target nucleic acids of interest occurring in in vivo and in vitro samples, including in cells, e.g. prokaryotic and eukaryotic cells. Examples of such target nucleic acids can be naturally occurring nucleic acids, such as a gene, a RNA, a tRNA, a mRNA, and pre-mRNA, a mature mRNA, a microRNA, a pre-microRNA, a mature microRNA, snRNA, piwi-interacting RNA (piRNA), pathogen-generated DNA or RNA, such as viral RNA or DNA or a sequence.

The Z-probes of the present invention can be used to detect and quantify metabolites of the target nucleic acids of interest, including but not limited to those that result from removal or modification of one or more of the nucleobases, removal or hydrolysis of one or more nucleotides from the 5' or 3' end, or fragments generated by non-specific endonucleases or by specific restriction enzymes, e.g. by breaking of the internucleoside linkages within the molecule, including by enzymatic digestion of DNA or RNA, or to detect products of phosphorylation of small nucleic acids, or various natural small nucleic acid conjugates with other biological molecules.

The Z-probes can be used to detect and quantify synthetic small nucleic acids or artificially introduced small nucleic acids, such as those expressed by vectors or by other genetic means or introduced by RNA transfection. Such synthetic or artificially expressed or introduced short nucleic acids can be oligotherapeutics, such as natural or modified ONs, ON conjugates or constructs containing ONs administrated to, or expressed in a sample, or in vivo for research, diagnostics, or for therapeutic purposes. Examples of such modality are antisense ONs, exon-skipping ONs, siRNA, aptamer, micro-RNA, small nucleic acid(s) that are part of the CRISPR technology, such as gRNA, targeting or guiding nucleic acids, or expression libraries, or any other nucleic acid conjugates used for selective targeting, specific transport, specific tissue targeting or distribution, pharmacokinetics modulation, nano-particles packing or formulation.

Z-probes introduced in a sample containing target nucleic acids selectively aggregate with their complimentary sequences to a significant degree if the melting temperature of the duplex is above the sample temperature, typically room temperature. There are methods, algorithms and software products for prediction of the hybridization strength, e.g. melting temperature of complementary sequences of different type of nucleic acids such as those described by M. Dumousseau et al. in "MELTING, a flexible platform to predict the melting temperatures of nucleic acids", BMC Bioinformatics, vol. 13, pages 101-113 (2012) and references sited therein. By using computational approaches and experimental techniques for measuring hybridization strength and melting temperatures of nucleic acids duplexes, the Z-probe sequences can be designed to hybridize completely with the nucleic acids of interest and at the same time have a minimal hybridization with non-complementary or miss-matched sequences under particular hybridization conditions such as sample temperature, ionic strength, particular ion concentration, and Z-probe concentration.

If the nucleic acid of interest is a duplex, e.g. siRNA or template dsDNA for CRISPR or hair-pin single stranded RNA, Z-probes can be designed to hybridize to both strands of the duplex, at adjacent or partially overlapping areas. Z-probes complimentary to both strands can be used separately or simultaneously.

The duplexes between the Z-probes and the small nucleic acids of interest can be separated from the excess of unhybridized Z-probes and from other nucleic acids present in the sample by using analytical techniques well known to one skilled in the art. Especially useful methods of separation are those that rely on the difference in the net negative charge of nucleic acids, such as ion-exchange chromatography, in particular ion-exchange HPLC (IE HPLC) or ion-exchange cartridges, or ion-pairing reversed phase HPLC, and gel electrophoresis (GE), in particular capillary gel-electrophoresis (CGE).

Retention under anion-exchange conditions decreases and the mobility under CE conditions decreases with the decrease of the net negative charge. Therefore, Z-probe hybrids with partial or complete backbone charge neutralization have higher mobility (lower retention) under anion-exchange conditions and lower mobility (higher retention) under CE conditions and Z-probe hybrids with complete charge neutralization would lose their retention or mobility, respectively. This simplifies the separation of an excess of Z-probes having partially of fully charge-neutralized backbones from their duplexes with the small nucleic acids of interest, which have fully negatively charged backbones.

Z-probes with net positive charge reduce the net negative charge of their duplexes with the negatively charged nucleic acids of interest, therefore facilitating the separation of those duplexes from non-complementary single or double stranded nucleic acids with a similar number of nucleotides. Moreover, Z-probes having high net positive charge can be used to analyze relatively large nucleic acids, which otherwise are difficult to analyze by ion-exchange HPLC because of their high net negative charge and high retention. The number and the type of CMGs attached to the backbones of the Z-probes can be modified in each particular case in order to provide for such a charge modification of the Z-probes and/or Z-probe duplexes with the nucleic acids of interest, which may assist in their separation from interfering components in the sample, which is one of the main advantages of the current invention as compared to the prior art.

In some embodiments of the present invention, Z-probes featuring CMGs together with groups or ligands with high specific binding affinity can be used for separation of the Z-probe duplexes, before their analysis, from any other non-complementary nucleic acids or any other components of the sample, by utilizing the specific high affinity binding of the Z-probe-attached group or ligand such as biotin or antigen to its counterpart, such as avidin or antibody immobilized to solid surfaces, columns, beads, or by other means generally known to one skilled in the art.

The reporter groups attached to the Z-probes can facilitate the detection of Z-probes duplexes with their complementary nucleic acid(s) of interest utilizing the reporter detection properties, such as, but not limited to fluorescence, light absorption or emission, nuclear or electron spin properties, high energy particles emission etc. Attachment of more than one reporter group to the Z-probe can be used to increase the sensitivity of the detection method and improve the limit of detection and quantification. In another embodiment of this invention, the use of different Z-probes, having different complementarity properties and bearing different reporter groups can be used for simultaneous detection and quantification of more than one small nucleic acid of interest in a single sample.

In some embodiments of the present invention, the hybridization of the Z-probe to the nucleic acid of interest can be detected and quantified without the need to separate the unhybridized Z-probe from its hybrid and from other small nucleic acids of interest by utilizing detection moiety attached to the Z-probe, which is sensitive to its environment and possesses specific detectable properties only when the Z-probe is hybridized to a complementary nucleic acid, as for instance fluorescent dye which shifts its emission wavelength or changes the intensity of its emission when it is a part of a nucleic acid duplex as opposed to a single stranded nucleic acid. In other embodiments, the detection of the Z-probe duplexes with the nucleic acid(s) of interest can be accomplished using mass-spectrometry.

This invention discloses a method for qualitative and quantitative detection of nucleic acids of interest, and particularly short nucleic acids of interest, occurring or administrated in a sample. Short nucleic acid(s) of interest can be naturally occurring or artificially expressed nucleic acids (e.g. DNA or RNA) or man-made oligotherapeutics. A method of the invention comprising the steps of 1) design and production of Z-probes complimentary to the nucleic acid(s) of interest, where the said Z-probes may, or may not have attached to them one or more reporter groups, or high specific binding moieties, and where the Z-probes enable formation of a duplex with the targeted nucleic acids with needed stability; 2) obtaining a sample (processed if needed) containing or suspected of containing the oligotherapeutics, naturally occurring or artificially introduced or expressed nucleic acid(s), modified ON, or their conjugates; 3) forming a hybridization duplex by contacting the Z-probe of step 1 with its complementary nucleic acid of interest from step 2; 4) separating the hybrids formed between the nucleic acid(s) of interest and Z-probes from unhybridized Z-probes and unhybridized, non-complementary or only partially complementary nucleic acids or other components of the sample by anion exchange high performance liquid chromatography, gel-electrophoresis, capillary gel-electrophoresis, anion exchange cartridge, or any other charge separation-based modality and/or by binding of the high affinity and specificity binding entity attached to the Z-probe (if such entity is used) to its counterpart and 5) qualitatively and/or quantitatively detecting said hybridized moieties by utilizing their specific properties, or utilizing the specific detection properties of the reporter groups which may be attached to the Z-probes, by means of fluorescence, or UV, or visible light spectroscopy, or radioactivity detection, or by mass spectrometry, or by other means specific for the particular Z-probe, small nucleic acid of interest or their duplex, or for particular reporter groups attached to the Z-probe.

The advantages of the present invention over other prior art are based on the special features enabled by the chemical architecture of the Z-probes having structure (I)/(IA) and by the backbone modifier groups attached at the targeted locations of the Z-probes and having structure (II)/(IIA).

Some examples of charge modifying groups are shown in the FIG. 1.

Figure 2:
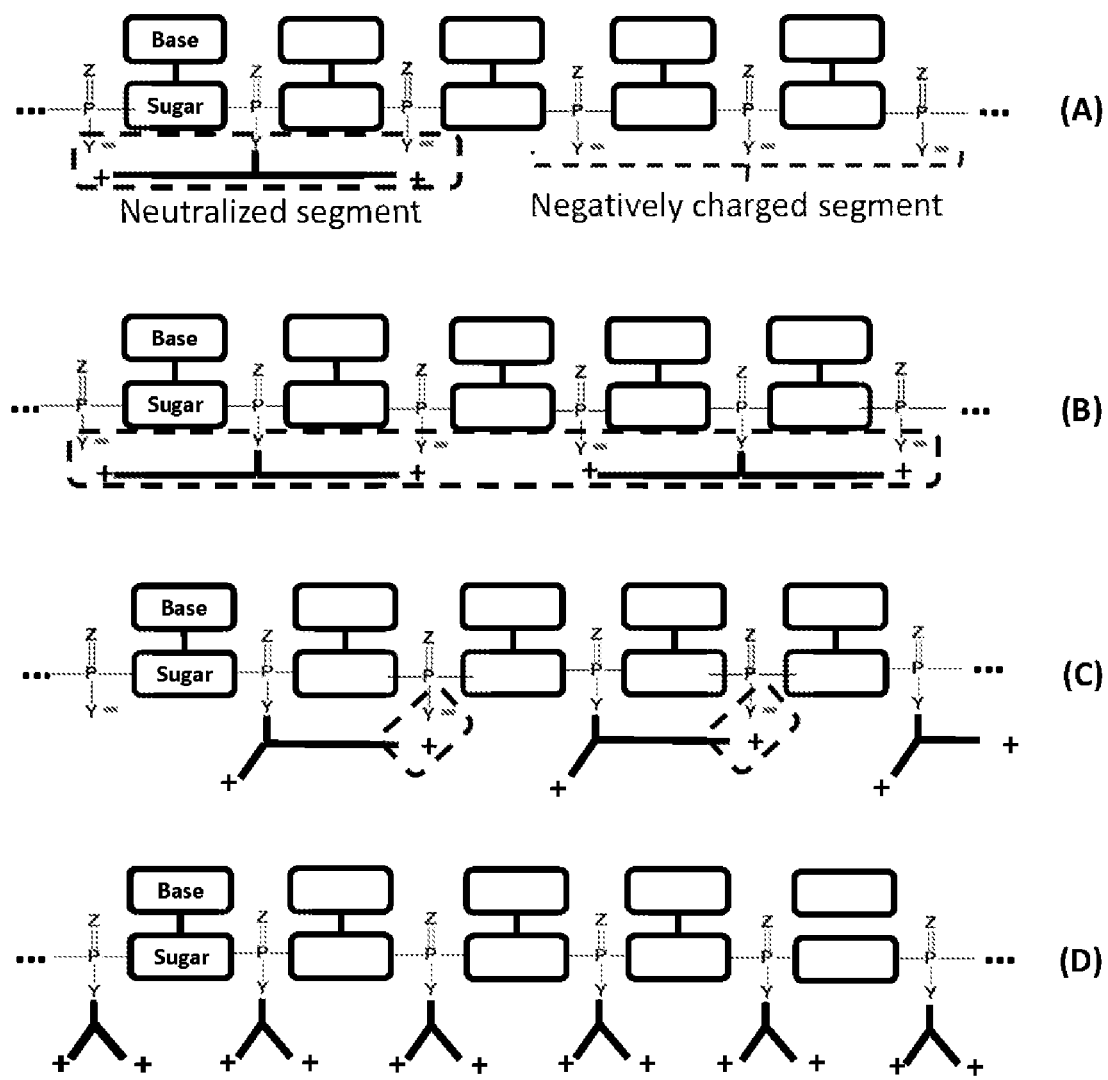
FIG. 2 shows a schematic representation of charge-modified oligonucleotides (Z-probes) having net charge variations provided by different charge modifying groups in the Z-probes and/or by the number of Z-probes attached to the oligonucleotide segment. The sugars can be any natural sugars occurring in DNA or RNA or modified analogs or sugar mimics existing in synthetic modified ONs. The bases can be uracil (U), thymine (T), cytosine (C), adenine (A), or guanine (G), or their analogs, or any other moiety capable of sequence specific base-pairing. Y and Z can be independently O or S. The symbols "+" and "−" stand for positive and negative charges, respectively. The oxygen atoms between the sugar and the phosphorus atoms are omitted for the purpose of easier visualization. The optional reporter moieties are not illustrated.
Figure 3:
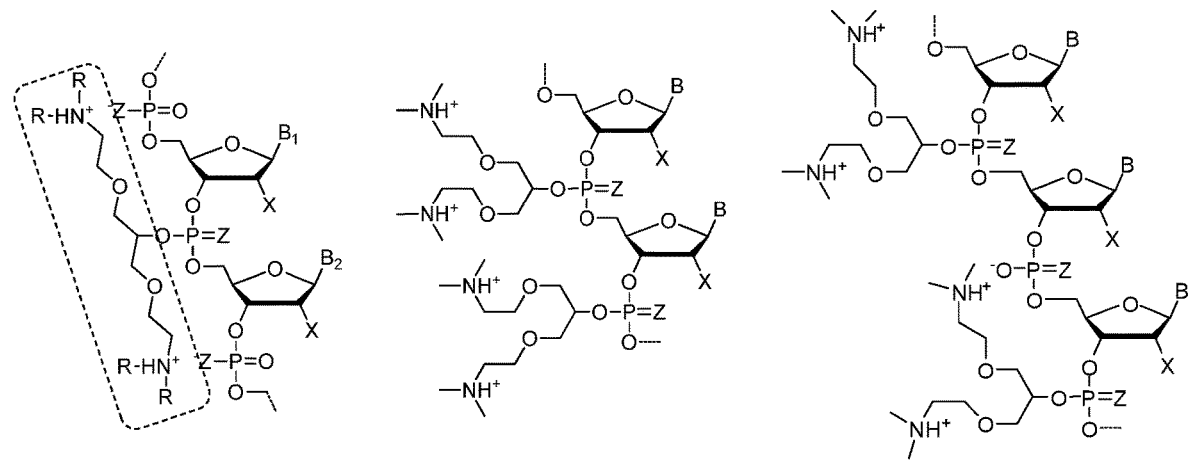
FIG. 3 shows exemplary segments of Z-probes containing CMGs attached to the internucleoside phosphates enabling different level of cationization.

In some embodiments, the number and structures of charge modifying moieties having structure (II) and illustrated in the examples of FIG. 1 can enable reduction or elimination of the net negative charge or introduction of a net positive charge to the Z-probe as it is illustrated in FIGS. 2 and 3.

In some embodiments, a Z-probe can comprise charge-modifying moieties at any number and any location in its backbone limited only by the numbers of internucleoside linkages.

Z-probes possess properties making them advantageous in comparison to other known oligonucleotide-based probes. For instance, Z-probes are highly soluble, with preserved or enhanced Watson-Crick hybridization properties, which can be modulated by varying the ionic strength of the medium, with increased serum and/or nucleases stability, and with the possibility of modifying the degree and the type of their net charge.

In some embodiments, the properties of Z-probes can be advantageously tuned by linking different charge modifying moieties possessing different features provided by structure (II) to the internucleoside linkages. Moieties of structure (II) (e.g. charge modifying moieties) enable symmetrical and asymmetrical charge modifying groups that can add 2, 3, 4, 5, 6, 8 or more positive charges to the Z-probe backbone.

Figure 4:
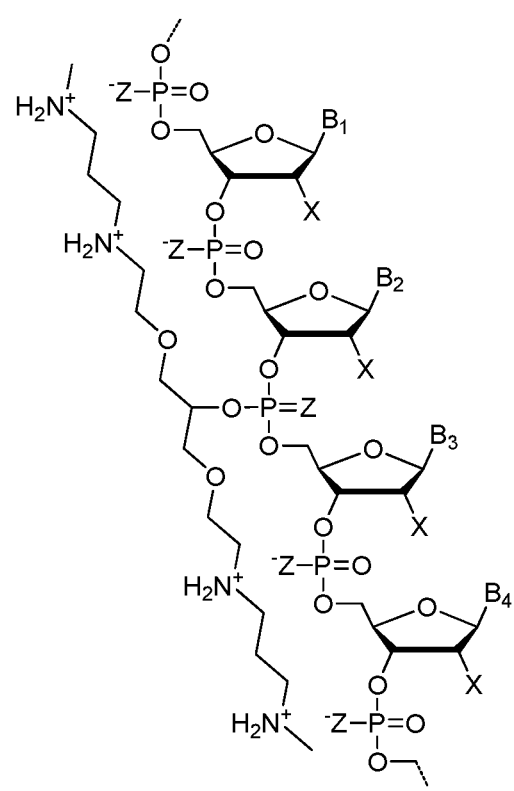
FIG. 4 shows a segment of 2'-OMe based Z-probes comprising CMG6 from FIG. 1 linked to the internucleoside phosphate and simultaneously forming four ion-pairs with the neighboring internucleoside phosphate groups. The CMG6 moiety is shown in its protonated form. B stands for the nucleoside bases and Z can be independently an oxygen or a sulfur atom. X can be hydrogen (H), hydroxyl (OH), methoxy (OMe), methoxyethyl (MOE), or Fluorine (F) moieties.

For example, charge modifying moieties in FIGS. 3 and 4 can eliminate 3 and 5 negative charges per a CMG, respectively.

Additionally, in some embodiments charge modifying moieties can contain different types of positively charge termini groups enabled by structure (II), e.g., primary, secondary, tertiary amino, or quaternary ammonium groups. It will be understood that positive charges due to presence of primary, secondary or tertiary amino groups will occur to a different degree depending on the medium and its pH.

In general, selection and spacing of charge modifying moieties can allow Z-probes to be cationized to a different degree as well as to be with partially or fully neutralized backbone.

By selecting the type, the number and the place of attachment of the CMGs, other Z-probe properties, in addition to their net charge, can be modified and optimized. For instance, by selecting different CMGs, a partial hydrophobicity can be introduced and this hydrophobicity can be used for development and optimization of reversed-phase based chromatographic methods for analysis of their duplexes with the small nucleic acids.

The synthesis of some of the CMGs having structure (II), the synthesis of phosphoramidite reagents that can be used for attachment of the CMGs to the Z-probe backbones during the automated synthesis and the methods for use of the phosphoramidites have been disclosed by Tabatadze and Yanachkov in WO2016/081600A1 and in "Self-neutralizing oligonucleotides with enhanced cellular uptake", Org. Biomol. Chem., vol. 15 (6), pages 1363-80 (2017), which are hereby incorporated in their entirety by reference.

Reporter groups, or high specific binding groups in structure (I) are linked to the 5' and/or 3' end and/or to any of the bases, and/or to the internucleotide linkages with or without spacers.

In some embodiments of structure (I), the reporter group can be the same or different reporter moiety, such as a fluorescein dye from the groups of fluorescein or substituted fluorescein dyes such as, but not limited to, 6-carboxyfluorescein, 6-carboxy-4',5'-dichloro-2',7'-dimethoxyfluoresceine (JOE), hexachlorofluoresceine (Hex) and 5-Tetrachloro-Fluorescein (TET), or from the group of the rhodamine dyes or variants thereof, such as Rhodamine Green and carboxytetramethylrhodamine (TAMRA), or from the group of the cyanine dyes or variants thereof, such as Cy5, Cy5.5, Cy3.3 and Cy3, or from other classes of fluorescent dyes, such as the coumarin group, or the xanthene group or Alexa Flour line of dyes. This list of different fluorescent dyes or classes of fluorescent dyes is not intended to be exhaustive and a person skilled in the art will recognize other fluorescent dyes that can be used as reporter groups, which will also be within the scope of the present invention.

In a preferred embodiment, the fluorescent reporter group has a high molar extinction coefficient and/or quantum yield. In a most preferred embodiment, the fluorescent reporter group is of high brightness, i.e. it has a high product of its molar extinction coefficient and its quantum yield.

The reporter group may be a fluorescent dye which is sensitive to its environment, i.e. it changes its fluorescent intensity, quantum yield, fluorescents wavelength, or the parameters of its fluorescent dynamics depending on the degree of hybridization of the Z-probe with its complementary ONs, or depending on other environmental parameters, such as pH, ionic strength, presence and concentration of different ions, dielectric constant or medium polarity.

In some embodiments, the reporter group can be a group that affects or changes the fluorescence of other groups, such as fluorescence a quencher.

In some embodiments, the reporter group may be a dye that absorbs light in the visible, or the near-visible infrared or the ultraviolet spectrum. In a preferred embodiment, the fluorescent reporter group has an absorption maximum in an area where the absorption of the sample components is minimal. In another preferred embodiment, the emission maximum of the fluorescent reporter group is in a spectral area where the components of the sample do not have or have a minimal fluorescent emission. Especially preferred are fluorescent probes with emission maximum in the longer wavelength visible, or near-infrared spectrum, where the autofluorescence of the biological systems is minimal.

In other embodiments, the reporter group may be a moiety with high affinity specific binding to another moiety, such as biotin, which has high specific affinity to avidin, or an antigen with a high specific binding to an antibody.

In other embodiments, the reporter group may be a chemical entity that contains radioactive isotopes, such as $^{35}S$, $^{31}P$, $^{14}C$, or $^{3}H$, $^{131}I$, $^{111}In$, $^{99m}Tc$ or other radio labels, which can be detected by their emission, for instance by using radioactivity detectors or in-line or off-line scintillation counters, or other detection systems, which are well known to one skilled in the art.

In some other embodiments, the reporter group may contain stable isotopes, such as $^{2}H$, $^{18}O$, $^{13}C$, $^{15}N$, the presence of which can be detected by using mass spectrometry, for instance high resolution mass spectrometry.

The attachment of the reporter group to the 3'-end of the Z-probe can be achieved during its synthesis by using control pore glasses (CPGs) with a pre-attached reporter group or high specific affinity group, which are specifically developed for attachment of reporter groups to ONs 3'-end and are commercially available from vendors such as Glen Research. Examples of such CPGs are 3'-Fluorescein CPG, 3'-(6-Fluorescein) CPG, 3'-(6-FAM) CPG, 3'-6-Fluorescein-Serinol CPG, Cyanine 3 CPG, Cyanine 5 CPG, Redmond Red® CPG, Yakima Yellow® CPG, AquaPhluor® 593 CPG, Eclipse® Quencher CPG, 3'-BHQ-1 CPG, 3'-BHQ-2 CPG, 3'-BHQ-3 CPG, BBQ-650® CPG, 3'-TAMRA CPG, 3'-TAMRA PS, 3'Dabsyl CPG, and 3' Dabcyl CPG.

Attachment of the reporter group to the 5'-termini of the Z-probe can be accomplish during its synthesis by using phosphoramidite reagents and protocols specifically developed for attachment of fluorescent dyes or affinity groups to the 5'-termini of ONs, and available commercially from vendors such as Glen Research. Examples of such reagents are 5'-Fluorescein Phosphoramidite, 5'-Hexachloro-Fluorescein Phosphoramidite, 5'-Tetrachloro-Fluorescein Phosphoramidite, SIMA (HEX) Phosphoramidite, Cyanine 3 Phosphoramidite, Cyanine 3.5 Phosphoramidite, Cyanine 5 Phosphoramidite, Cyanine 5.5 Phosphoramidite, Redmond Red® Phosphoramidite, Yakima Yellow® Phosphoramidite, 5'-AquaPhluor® 593 CE Phosphoramidite, Eclipse® Quencher Phosphoramidite, 5'-BHQ-1 Phosphoramidite, 5'-BHQ-2 Phosphoramidite, 5'-BBQ-650®-CE Phosphoramidite, and 5' Dabcyl Phosphoramidite.

The reporter groups can be attached to the nucleobases of the ONs, preferably to the C5 of the pyrimidines and C8 of the purine bases. This attachment can be done during the automated synthesis using commercially available phosphoramidites, such as Dabcyl-dT Phosphoramidite, Fluorescein-dT Phosphoramidite, SIMA (HEX)-dT Phosphoramidite, BHQ-1-dT Phosphoramidite, BHQ-2-dT Phosphoramidite, BBQ-650®-dT-CE Phosphoramidite, and TAMRA-dT Phosphoramidite. The attachment can be done post-synthetically using, for instance, synthetic ONs containing one or more amino group(s) connected to the C5 of some of the pyrimidine bases. Such ONs can be prepared by standard automated synthesis using commercially available phosphoramidites containing protected amino-group terminated linker at C5 of the pyrimidine base or C8 of the purine base, such as Amino-modifier C2 dT (cat. no. 10-1037-90) or Amino-modifier C6 dT (cat. no. 10-1039-90) or Amino-modifier C6 dC (cat. no. 10-1019-90) or Amino-modifier C6 dA (cat. no. 10-1089-90) from Glen Research. Reporter groups can be attached post synthetically to the amino-group terminated linker by using amino-group reactive activated fluorescent dye or biotin derivatives, such as N-hydroxysuccinimidyl esters, isothiocyanates or sulfonyl chlorides available commercially from ThermoFisher Scientific and general coupling method well known to one skilled in the art.

Alternatively, the attachment of reporter groups to the nucleobases can be done post synthetically using C5 ethynyl functionalized pyrimidine bases, which can be introduced in the ONs using commercially available C5 ethynyl amidites such as 5-Ethynyl-dU-CE Phosphoramidite (Cat. No. 10-1554-xx) available from Glen Research. The post synthetic coupling of the reporter group can be accomplished by using commercially available azide derivatives of fluorescent dyes or biotin by the Click Chemistry approach as described by H. C. Kolb et al. in Angew. Chem. Int. Ed., volume 40 (11) pages 2004-2021 (2001) and as disclosed by WO2008052775A2.

The reporter groups can be attached to the internucleoside linkages as disclosed by Tabatadze et al. in U.S. Pat. No. 8,084,589 and in Nucleosides Nucleotides Nucleic Acids, vol. 27 (2), pages 157-172 (2008) and by Zang et al. in Proc. Natl. Acad. Sci. USA, vol. 105 (11), pages 4156-61 (2008) which are incorporated in their entirety herein by reference.

The sample containing or suspected of containing nucleic acid(s) of interest, including modified ONs, can be obtained from cell cultures, including cell cultures exposed to nucleic acids or modified ONs, or exposed to modalities that can induce expression of the small nucleic acids (in vitro) or from an organism, including an organism that has been administered in vivo with small nucleic acids, including modified ONs, or with modalities causing in vivo expression of the small nucleic acids of interest. The samples following in vivo administration can, for example, be blood, plasma, urine or other biological fluids, or tissue isolated from an animal or a plant. Non-limiting examples of tissue samples are adipose tissue, bone marrow, brain, cartilage, cancer cells, heart, immune cells, intestine, kidney, liver, lung, muscle, neurons and pancreatic cells, or different plant tissues.

In some embodiment, the sample containing cells or tissues is treated for cell/tissue disruption and homogenization using physical methods such as grinding, shearing, bead beating, shocking, freezing and ultrasound and/or chemical methods, such as lytic enzymes, chaotropic agents, and different types of detergents.

In a preferred embodiment, the sample, or the treated (homogenized) sample is subject to liquid-liquid or solid phase extraction or precipitation. Methods for liquid-liquid or solid phase extraction or precipitation of nucleic acids are well known to one skilled in the art and may include, without being limited to, phenol-chloroform extraction with or without guanidinium thiocyanate, cetyltrimethylammonium bromide extraction, alkaline extraction, cesium chloride (CsCl) gradient ultracentrifugation (with or without ethidium bromide), Chelex® extraction, and a large variety of solid-phase extraction (SPE) methods using either normal phase, reversed-phase, ion-exchange, cellulose or other type of absorption matrixes as summarized by Ali et al. in "Current Nucleic Acid Extraction Methods and Their Implications to Point-of-Care Diagnostics", Biomed. Res. Int. 2017: 9306564, doi: 10.1155/2017/9306564 and in the references cited therein.

In some embodiments, the sample can be treated with an organic solvent, reagent, acid, enzyme inhibitor, or proteinase prior to addition of the Z-probe, that can inactivate/remove proteins from the sample and prevent potential degradation of the nucleic acid of interest by enzymes present in the sample. In other embodiments, the sample may be treated for selective removal of one or another type of nucleic acid(s). For example, the sample may be treated with DNase, such as Deoxyribonuclease I to selectively degrade DNA if the nucleic acid of interest is RNA or modified ONs resistant to DNases. In other embodiments, the sample may be treated with RNases if the nucleic acids of interest are DNA. In yet another embodiment, the sample may be treated with nucleases that degrade oligo and polynucleotides, if the nucleic acid of interest is a modified ON that is resistant to the said nucleases. In addition, the sample may also be subjected to centrifugation, dialysis, ultrafiltration and to any other procedure intended to remove sample components and enrich the sample to and to stabilize the nucleic acids of interest.

In some embodiments, after addition of the Z-probes to the sample, the sample is subject to annealing by heating to a certain temperature for a pre-determined time and then applying gradual cooling at a predetermined rate. Such annealing processes may be used to disrupt any pre-existing duplexes or secondary structures in which the nucleic acid(s) of interest may be involved, and to facilitate the complete formation of duplexes between the Z-probes and their complementary nucleic acid(s) of interest. The exact parameters of this annealing process (temperature, time and rate of cooling) are chosen considering the melting temperatures of any pre-existing duplexes and secondary structures involving the small nucleic acid(s) of interest and the melting temperatures of their duplexes with the Z-probes.

In some embodiments, the separation of the duplexes of the Z-probes from the unhybridized Z-probes and from any other components of the sample is preferably performed using ion-exchange HPLC (IE-HPLC). A number of commercially available anion-exchange HPLC columns such as those manufactured by Dionex, part of ThermoFisher (DNAPac PA100, DNAPac PA200), Shodex (QA-825), Tosoh Bioscience (TSKgel DNA-NPR, TSKgel DNA-STAT, TSKgel SuperQ-5PW, TSKgel BioAssist Q), Hamilton Robotics (PRP-X100, PRP-X110, PRP-X500) or Waters (Gen-Pak FAX), which are specifically designed for separation of ONs and small nucleic acids, as well as anion-exchange column of USP designation classes L14, L23, L31, L47, L48 and L74 can be used for the analysis of Z-probes duplex(es) with complimentary nucleic acid(s) of interest.

Elution buffers and HPLC gradients are selected according to the column in use. In some embodiments the elution buffer comprises aqueous salt solutions, such as Sodium perchlorate ($NaClO_4$), Sodium Chloride (NaCl) or Lithium Chloride (LiCl) in concentrations or gradients from 0.01 to 3 M, which may be buffered with Tris-HCl, phosphate, or other suitable buffers. Complexing agents, such as EDTA or DTPA in concentrations from 0.1 to 100 mM and preferably from 1 to 10 mM can be present to prevent interference from divalent or polyvalent metals present in the sample. Organic solvents such as methanol or acetonitrile in concentrations from 0.001% to 75%, and preferably from 1% to 25%, may also be present to prevent unwanted secondary interactions with the column matrix. The column temperature may be regulated from 0 to 100° C., preferably between about 10 to 60° C., or the column may be at ambient temperature. A person skilled in the art will recognize other suitable HPLC columns and elution/separation methods, and to optimize them for the purpose of the present invention.

In another preferred embodiment, the detection and quantification of the duplexes of the nucleic acids of interest with Z-probes containing fluorescent reporter groups during their HPLC analysis is done by fluorescence detectors. The fluorescence detectors can be in-line detectors connected to the output of the HPLC system and can be off-line fluorescence spectrometers that can be used to measure the fluorescence of individual fractions after HPLC separation. Various in-line HPLC fluorescence detectors are available commercially from HPLC systems manufacturers, such as Waters Inc., Agilent, Shimadzu, ThermoFisher and Perkin-Elmer. If the Z-probe is labeled with two or more different fluorescent probes, or if two or more different Z-probes are used for multiplexing analysis, then a multichannel detector, which may excite and detect simultaneously at two or more wavelengths can be used. Alternatively, for the same purposes, more than one single wavelength detector can be connected in series.

In yet another embodiment, the detection and quantification of the duplexes of the nucleic acids of interest with Z-probes which do not contain reporter moieties can be accomplished using UV single wavelength, multiple wavelengths or diode array detectors and observing the UV absorption of the nucleobases of the duplexes. Such detection methods are well known to one skilled in the art.

In another embodiment, the detection and quantification of the duplexes of the nucleic acids of interest with Z-probes which are labeled with radioactive isotopes is accomplished after their chromatographic analysis using radioactivity detectors. Such detectors can be either in-flow-through configuration or off-line scintillation counters. The in-flow (on-line) detectors can be either through in-flow detectors or stop-flow type detectors. The off-line detectors can be vial-type scintillation counters, or, preferably, microplate solid scintillation counters, such as TopCount NXT (Perkin-Elmer).

The Z-probes that will be subject to radioactivity detection can be labeled with radioactive isotopes, such as $^{31}P$, $^3H$, $^{14}C$, $^{35}S$, $^{131}I$, $^{111}In$ or $^{99m}Tc$. The labeling with $^{31}P$ can be achieved post-synthetically using $\gamma$-$^{31}P$-adenosine 5'-triphosphate and T4 polynucleotide kinase (Ambion® KinaseMax™ kit from ThermoFisher or alternative kits). The $^{14}C$ labeling can be accomplished using commercially available $^{14}C$ labeled nucleoside phosphoramidites (Moravek, Inc. Brea, CA) and as described by Guzaev at al. in Nucleosides and Nucleotides, Vol. 18 (6-7), pages 1389-1390 (2006) and by Sasmor et al. in Journal of Labelled Compounds and Radiopharmaceuticals, vol. 36 (1), pages 15-31 (1995). Tritium labeled Z-probes ca be prepared post-synthetically by exchange of C8 purine hydrogens using tritiated water as described by Graham et al. in Nucleic Acids Research, vol. 21 (16), pages 3737-3743 (1993), or by other post-synthetic methods (Ledoan et al., Nucleosides and Nucleotides, vol. 18 (2), pages 277-289 (1999); Christensen et al., Journal of Labelled Compounds and Radiopharmaceuticals, vol. 55 (6), pages 189-196 (2012)). Labeling with $^{35}S$ of phosphorthioate Z-probes can be achieved during their automated synthesis by sulfurization with $^{35}S$ labeled sulfurizing reagents as disclosed in EP0790965A1. Z-probes can be labeled with other radio-nuclei, such as $^{131}I$ (by iodination) or by attachment of chelators for metal radioisotopes, e.g. $^{111}In$ or $^{99m}Tc$. A person skilled in in the art can recognize other ways and modes of radiolabeling of the Z-probes for use in the method of the present invention.

In another preferred embodiment, the separation and analysis of the duplexes of the Z-probes with the nucleic acids of interest can be performed by gel-electrophoresis. For instance, agarose or polyacrylamide gels can be used for the separation of Z-probes from Z-probe hybrids with their complementary nucleic acids of interest and from nonhybridized nucleic acids utilizing the differences of the net charge and the cross-section of those species. The agarose gel concentration can be from 0.05 to 5%, preferably from 0.5% to 3% with Tris/Acetate/EDTA, TRIS/Borate/EDTA or lithium borate/EDTA or MOPS buffers, bromophenol blue and xylene cyanol loading dyes and from 0.5 to 10 V/cm voltage. Typical PAGE (polyacrylamide gel electrophoresis) condition can be: 3% to 30% acrylamide, preferably from 6% to 20% acrylamide, 1% to 2% bisacrylamide and Tris/borate/EDTA buffer.

Typical equipment and methodology used for gel-electrophoresis of DNA and RNA and ONs can be applied, and selection of particular equipment and conditions is within the skills of one skilled in the art. The visualization/detection and quantification of the duplexes of the Z-probes with the small nucleic acids of interest can be accomplished by standard visualization methods used in GE of nucleic acids, such as ethidium bromide/UV light. Alternatively, specific fluorescence or radio imaging methods can be used if the Z-probes are labeled with fluorescent reporter groups or with radionuclides.

In some preferred embodiments, capillary electrophoresis (CE) is used for the separation and detection/quantification of the duplexes of the Z-probes with the nucleic acids of interest. The CE can be performed preferably as capillary gel-electrophoreses (CGE) with polyacrylamide gels and with, but without being limited to, buffers such as Tris/borate/EDTA buffer. Standard, pre-fabricated capillaries can be used. In a preferred embodiment, the capillary and the buffer are selected as to reduce or completely eliminate the electroosmotic flow. The detection of the separated duplexes of the Z-probes with the nucleic acids of interest is done either by standard UV detection, or by fluorescent or radio-activity detectors.

The detection of the nucleic acids of interest can be performed by using ion-exchange cartridges. Cartridges, prepared, for instance, from common anion-exchange materials, e.g. diethylamino ethyl (DEAE) bonded support can be used for a manual or liquid chromatography approach. For instance, a cartridge filled with DEAE beads can be primed by low concentration NaCl or $NaClO_4$ buffered solutions at neutral pH, and a water-based extract from a sample comprising a suspected duplex loaded on the cartridge. The excess of Z-probes with low net negative charge, without net charge (neutral), or with net positive charge can be eluted from the cartridge with a low ionic-strength buffer. The duplexes of interest can then be eluted with a high ionic strength buffer and quantified spectroscopically. The skilled person in the art will recognize how to optimize the type and the size of the cartridge and the type, concentrations and volume of the buffers to be used in the above embodiment. Cartridges can be purposely developed for the method of the present invention or obtained from commercial sources, such as Phenomenex (Torrance, CA), Waters Corp. (Milford, MA) or ThermoFisher Scientific.

In another embodiment, the detection and quantification of the duplexes of the Z-probes with the nucleic acids of interest can be performed by using mass-spectrometry, preferably by electrospray ionization mass-spectrometry, and even more preferably by using high resolution mass-spectrometry, with or without chromatography separation. For mass-spectrometry based detection, Z-probes with or without reporter moieties can be used. In addition, Z-probes having stable isotopes, such as $^{13}C$, $^{15}N$, $^{18}O$, or preferably $^2H$ can be used. Such Z-probes can be prepared by using commercially available phosphoramidites labeled with stable isotopes, or by post-synthetic exchange as described above for radionuclides. The analysis can be done using quadrupole or ion-trap mass analyzer-based instruments or, preferably, time-of-flight or Orbi-Trap® mass analyzer-based instruments. Either single or multiple charged ions can be used for detection. In a preferred embodiment, before mass-spectrometry analysis, the sample solution is subjected to desalting and reducing of the solution ionic strength. This increases the Z-probes duplex stability (due to the effect of their charge neutralizing groups) and increases the mass-spectrometer ionization efficiency and sensitivity.

In some embodiments of the invention, the quantification of the nucleic acids of interest is done by using serial dilutions of synthetic standards of the nucleic acids of interests in sample medium. The standards are treated and annealed with Z-probes in the same way as the analysis samples and used to determine the detector response/concentration ratios and calibration curves. In other embodiments, internal standards of synthetic nucleic acids analogs are added to the analyses samples and used to quantify the nucleic acids of interest.

The presence of charge-modifying moieties in Z-probes provides for a convenient means for control, modulation and optimization of their hybridization strength (melting temperature) with complementary nucleic acids. The hybridization strength of the Z-probes having charge modifying moieties attached to their internucleoside linkages depends on the ionic strength of the buffer (medium). It increases with the lowering of the buffer ionic strength. Therefore, control of the hybridization (annealing) buffer ionic strength provides means for controlling the melting temperatures of the hybrids with the target nucleic acids of interest, and those with the miss-matched (off target) nucleic acids. For example, one can adjust the annealing buffer ionic strength in a way to provide for the melting temperature of the hybrids of interest to be sufficiently above the medium temperature and that of the Z-probes hybrids with mis-matched sequences to be sufficiently below the medium temperature as to provide for a maximum discrimination between the complementary sequences and the hybrids resulting from miss-matched sequences.

The advantages of the present invention over the known small nucleic acid quantitation methods are based, at least in part, on the special features of Z-probes that enable the variation of the type and the net number of the Z-probe charges. By changing the type and the number of the attached CMGs to the backbone of the Z-probes, their net negative charge can be changed from decreasingly negative to neutral and to increasingly positive. Such examples of Z-probes with variation of their net negative charge are demonstrated in FIG. 2 and in FIGS. 3 and 4, where two different backbone modifier groups (CMG5 and CMG6 from FIG. 1) containing segments are shown. Such wide variability of the type and the net number of the charges of the Z-probes is an advantage of the method of the invention since it enables the optimization of the detection and quantification of a wide variety of nucleic acids of interest in different types of samples. For instance, the variability of the net negative or positive charge of the Z-probes may result in changes of the mobility and the retention time of the resulted duplexes with the nucleic acids of interest, which allows for optimization of the IE, GE, or CGE chromatographic methods, and for avoidance of overlapping co-eluting sample components. The use of Z-probes with large net positive charge may allow for the analysis of relatively large nucleic acids by IE chromatography that otherwise will be problematic because of their significant retention due to their large net negative charge.

The sections below contain examples of nucleic acids of interest as well as the examples of Z-probes and control ONs and methods for their use relating to the methods of detection described above. The examples serve for illustrating purposes, and do not restrict the scope of the present invention and the applicability of the Z-probes and the methods of their use for detection of nucleic acids of interest described above.

EXAMPLES

Some examples of Z-probes and control ONs are listed in Table 1. Some methods of their synthesis are disclosed, in part, in Yanachkov et al., "Self-neutralizing ONs with enhanced cellular uptake", Org. Biomol. Chem., vol. 15 (6), pages 1363-80 (2016), which are hereby incorporated by reference.

TABLE 1

Examples of Z-probes and control ONs.

| Seq. No. | Sequence (5'>3') | Ribose modification |
|---|---|---|
| 1 | UGG ACC CUU AGA AAG UAG UAU CU | RNA |
| 2 | A$\underline{U}$A C$\underline{U}$A C$\underline{U}$U UC | 2'OMe |
| 3 | AUA CUA CUU UC | 2'OMe |
| 4 | UGG ACC CUU AGA AAG GAG UAU CU | RNA |
| 5 | A$\underline{U}$A C$\underline{U}$A C$\underline{U}$U U | 2'OMe |
| 6 | TAG AAA GTA GTA TCT | DNA |
| 7 | Cy5-C$\underline{A}$C $\underline{A}$AA $\underline{U}$UC GG$\underline{U}$ UC$\underline{U}$ ACA GG$\underline{G}$ UA | 2'OMe |
| 8 | Cy5-AG$\underline{A}$ G$\underline{U}$U C$\underline{U}$G UGG AAG $\underline{U}$CA A | 2'OMe |
| 9 | UAC CCU GUA UAA CCG AAU UUG UG | RNA |
| 10 | UU$_f$G A$_f$CU$_f$ UC$_f$C A$_f$CA$_f$ GA$_f$A C$_f$UC$_f$ U | 2'OMe and 2'F |
| 11 | A$\underline{U}$A C$\underline{U}$A C$\underline{U}$U UC | 2'OMe |
| 12 | Cy3-A$\underline{U}$A C$\underline{U}$A C$\underline{U}$U UC | 2'OMe |
| 13 | Cy3-AG$\underline{A}$ G$\underline{U}$U C$\underline{U}$G UGG AAG U | 2'OMe |
| 14 | UAG ACU UCC ACA GAA CUC U | 2'OMe |
| 15 | Cy3-AG$\underline{A}$ G$\underline{U}$U C$\underline{U}$G UGG A$\underline{A}$G $\underline{U}$CU A | 2'OMe |
| 16 | UGG ACU CUG AGA AAG GAG UAU GU | RNA |
| 17 | $\underline{A}$CA $\underline{U}$AC $\underline{U}$CC $\underline{U}$UU C$\underline{U}$C $\underline{A}$GA G$\underline{U}$C $\underline{C}$A | 2'OMe |
| 18 | ACA UAC UCC UUU CUC AGA GUC CA | 2'OMe |

In Table 1 above, 2'OMe means 2'-O-methyl and 2'F means 2'-fluoro-2'-deoxy sugar modifications. All internucleoside linkages are phosphodiesters. Underlined nucleotides (e.g., $\underline{U}$, $\underline{A}$) indicate the locations of the charge-modifying moieties (CMGs) which are attached to the 3'-phosphate. The CMGs have the structure of CMG5 from FIG. 1. Cy5 and Cy3 mean Cyanine 5 and Cyanine 3, respectively, reporter group introduced using Cyanine 5 Phosphoramidite catalog no. 10-5915-xx from Glen Research. The "f" subscript (e.g., U$_f$, G$_f$) indicates the nucleotides having 2'-fluoro-2'-deoxy modifications.

Example 1

Selective Hybridization Properties of Z-Probes

The purpose of this example is to demonstrate the preservation of the selective Watson-Crick hybridization properties of the Z-probes with DNA and RNA ONs. The selective hybridization of the Z-probes with high sequence specificity is a key property which enables the detection and quantification of small nucleic acids of interest.

Figure 5:
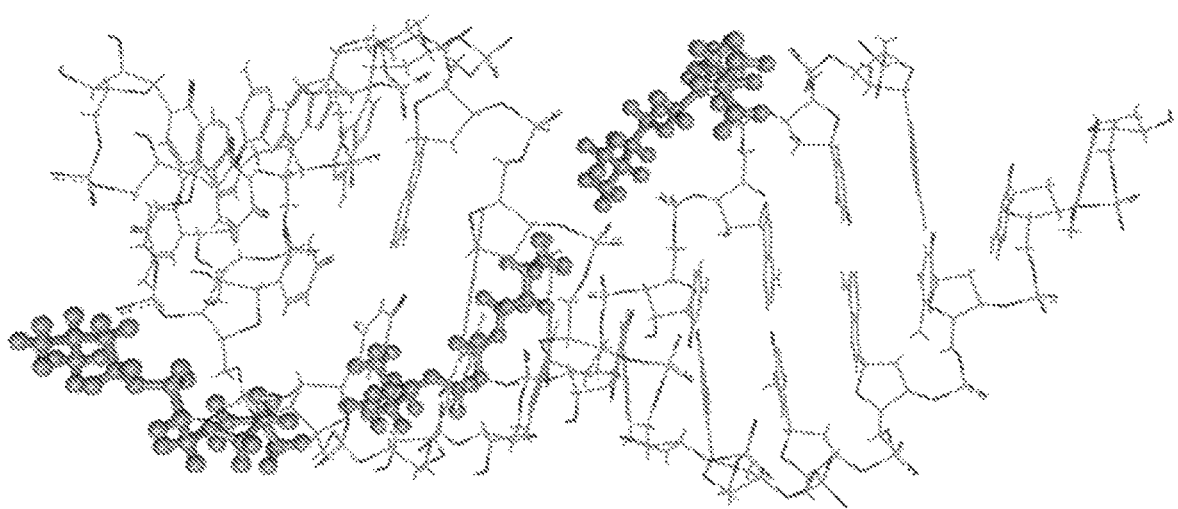
FIG. 5 shows a molecular model of duplex formation between DNA ON (Seq. 6, Table 1) and 2'-OMe based Z-probe (Seq. 2, Table 1) using MOE. Three CMG5 charge modifying moieties are linked to the Z-probe internucleoside phosphates.

Computer modeling (MOE Software) of a duplex between a Z-probe (Seq. 2) and complementary DNA ON (Seq. 6) is shown in FIG. 5. The model indicates that the three CMGs, attached to pos. 2, 5 and 8 (from 5') do not interfere with the formation of Watson-Crick type H-bonding and base pairing between the Z-probe and its complementary ON.

The sequence specificity of the hybridization of the Z-probes was determined experimentally by measuring the melting temperatures, $T_m$ of their duplexes with complementary or partially mis-matched DNA or RNA ONs. The $T_m$ were measured in two different media: one with low ionic strength (0.01 M sodium phosphate, pH 7.4) and another with high ionic strength (0.15 M NaCl plus 0.01 M sodium phosphate, pH 7.4). The tested duplexes, the media, and the observed $T_m$ are shown in Table 2.

Comparing of the $T_m$ of the duplex of a Z-probe (Table 1, Seq. 2, 2'-OMe 11-mer, 3 CMGs) with its complementary DNA (Table 1, Seq. 6, 15-mer) with that of a control ON, having the same sequence and chemistry but no CMGs (Table 1, Seq. 3, 2'-OMe 11-mer, no CMGs) demonstrates strengthening of the hybrid containing CMGs in both high and low ionic strength media (32 vs. 27° C. in high ionic strength media and 30 vs. <5° C. in low ionic strength media). Hybridization of the same Z-probe with a complementary RNA (Table 1, Seq. 1, 23-mer) resulted in no change of the $T_m$ of Seq. 1 and Seq. 2 hybrids (both hybrids melted at $T_m$ of 49° C.) in high ionic strength media. At the same, in low ionic strength media, the hybrid containing 3 BMSs (Seq. 2) showed significant strengthening of the duplex ($T_m$ increase by 14° C.) as compared to a control (Seq. 3) containing no CMGs ($T_m$, 45 vs. 31° C.), indicating that the CMG modifications increase the hybridization strength, at least in low ionic strength media.

The high sequence specificity of the hybridization of the Z-probes was demonstrated by hybridization of Seq. 5 from Table 1 (10-mer 2'OMe ON containing 3 CMGs) with its complementary 23-mer RNA (Seq. 1 from Table 1) and with complementary RNA, which contains one mismatch (Seq. 4 from Table 1). The observed melting temperature of the resulted hybrids are shown in Table 2. The hybrid of Seq. 5 with its fully complementary RNA (Seq. 1) showed slightly higher $T_m$ in high ionic strength buffer, then in low ionic strength buffer (41.6 vs. 38.9° C.). At the same time, no melting was observed down to 10° C. in both types of media with the hybrid of Seq. 5 with its complementary RNA (Seq. 4), which contained one mismatch (G vs A) at the middle of the complementary region, demonstrating the high sequence specificity of the hybridization of the Z-probes.

These data enables the conclusion that the Z-probes hybridize with high and sequence specific affinity to both DNA and RNA and that in a low ionic strength media the hybrids of the Z-probes are significantly stronger than those of the control ONs, which do not contain CMGs.

TABLE 2

T$_m$ of Z-probes with naturally occurring complementary, or partly mismatched DNA and RNA ONs.

| Duplex | Media | T$_m$, ° C. |
|---|---|---|
| Seq. 6 (DNA) × Seq. 2 (3 CMGs) | 0.15M - NaCl | 32 |
| 11 b.p. | 0.01M - NaPO$_4$ | 30 |
| Seq. 6 (DNA) × Seq. 3 (no CMGs) | 0.15M - NaCl | 27 |
| 11 b.p., control | 0.01M - NaPO$_4$ | <5 |
| Seq. 1 (RNA) × Seq. 2 (3 CMGs) | 0.15M - NaCl | 49 |
| 11 b.p. | 0.01M - NaPO$_4$ | 45 |
| Seq. 1 (RNA) × Seq. 3 (no CMGs) | 0.15M - NaCl | 49 |
| 11 b.p. control | 0.01M - NaPO$_4$ | 31 |
| Seq. 1 (RNA) × Seq. 5 (3 CMGs) | 0.15M - NaCl | 41.6 |
| 10 b.p. | 0.01M - NaPO$_4$ | 38.9 |
| Seq. 4 (RNA) × Seq. 5 (3 CMGs) | 0.15M - NaCl | <10 |
| 10 b.p., 1 mismatch | 0.01M - NaPO$_4$ | <10 |

Similar patterns were demonstrated when Z-probes were hybridized with modified ONs, particularly 2'OMe modified ONs. These data are disclosed by Yanachkov et al. in "Self-neutralizing ONs with enhanced cellular uptake", Org. Biomol. Chem., vol. 15 (6), pages 1363-80, which are hereby incorporated by reference. The data presented therein also shows that no melting was observed when CMGs containing ONs were annealed with non-complementary ONs, indicating that the CMG modification does not result in non-sequence specific aggregation.

Example 2

Effect of Reporter Group on the Hybridization Properties of the Z-Probes

Figure 6:
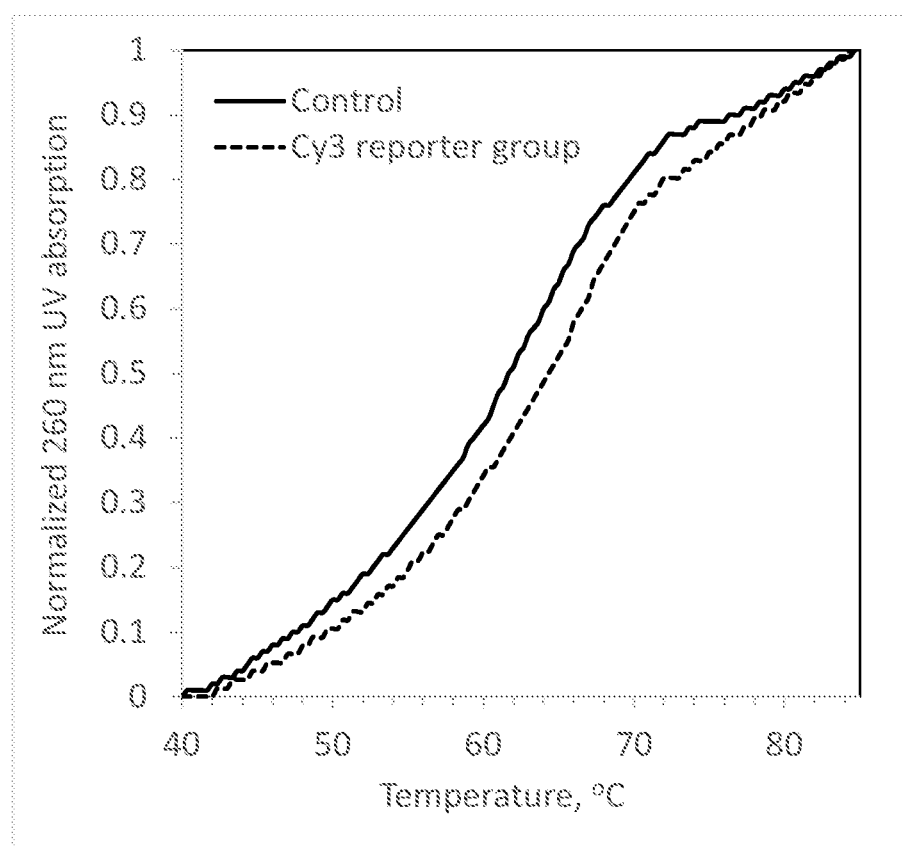
FIG. 6 provides the melting curves of duplexes of Z-probe comprising a Cy3 reporter group and a control ON without a reporter group with complementary RNA in 10 mM phosphate buffer (e.g., low ionic strength buffer).
Figure 7:
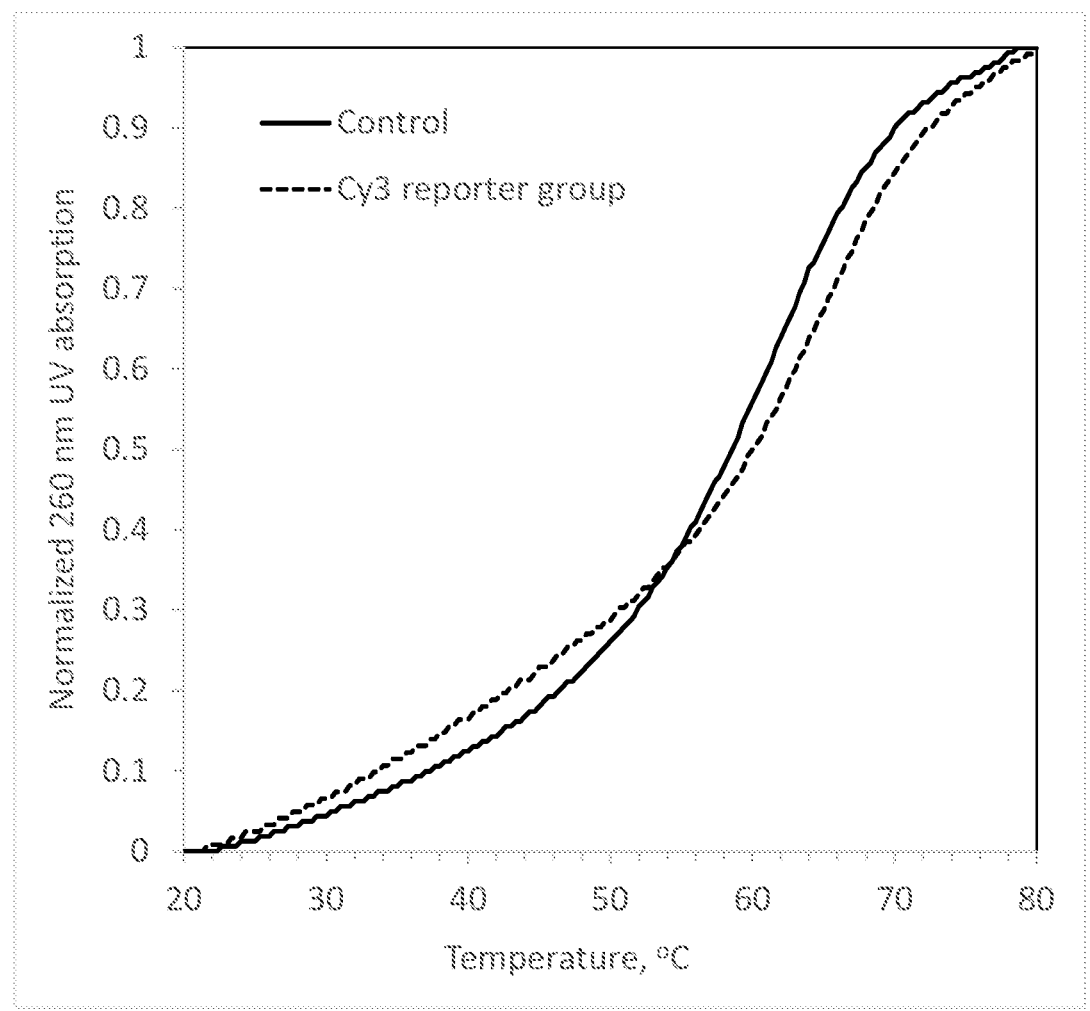
FIG. 7 provides the melting curves of duplexes of Z-probe comprising a Cy3 reporter group and a control ON without a reporter group its complementary RNA in 10 mM phosphate buffer and 150 mM NaCl (e.g., high ionic strength buffer).

The purpose of this example is to demonstrate that reporter groups do not interfere with the hybridization of the Z-Probes with the targeted nucleic acids. For that purpose, a 2'-OMe 11-mer Z-probe ON having 5 CMG groups (CMG5 from FIG. 1) and a Cyanine 3 fluorescent die (Cy3) as a reporter group attached to its 5' end (Seq. 12, Table 1) and an ON with the same structure but without a reporter group as a control (Seq. 11, Table 1) were annealed with their complementary RNA (Seq. 1, Table 1) and the resulted duplexes were subjected to melting study in both low ionic strength buffer (0.010 M sodium phosphate) and high ionic strength buffer (0.010 sodium phosphate and 0.15 M sodium chloride). The resulted melting curves are presented in FIGS. 6 and 7 and show that the reporter group (Cy3 fluorescent die) does not interfere with the hybridization of the Z-probe with its complementary RNA target.

Example 3

Detection of Synthetic ON Using Complimentary Z-Probe

The purpose of this example is to demonstrate the hybridization of a Z-probe with a complimentary synthetic 2'-O-Me RNA, the separation of the formed duplex from the excess of Z-probe by IE chromatography and its detection using a fluorescent detector. Another purpose of this example is to show the advantages which Z-probes provide for the separation of their duplexes with the target nucleic acids from the excess of the Z-probe.

Nineteen-mer synthetic 2'-O-Me RNA (Seq. 14, Table 1) was annealed with excess of its complementary 19-mer 2'-O-Me Z-probe labeled with Cy3 on its 5' termini and comprising 6 charge modifying moiety (CMG5 from FIG. 1) on the internucleoside linkages (Seq. 15, Table 1) by incubation of 10 pmols of Seg. 14 with 20 pmols of Seq. 15 in 200 µL hybridization buffer (HB, 10% ACN, 50 mM Tris-HCl, pH 7.5) at 90° C. for 15 min, then at 50° C. for 15 min and at room temperature for 60 min. Twenty microliters of this solution (1 pmol of Seq. 14 and 2 pmol of Seq. 15) were subjected to HPLC analysis by the method of this invention described herein.

Figure 8:
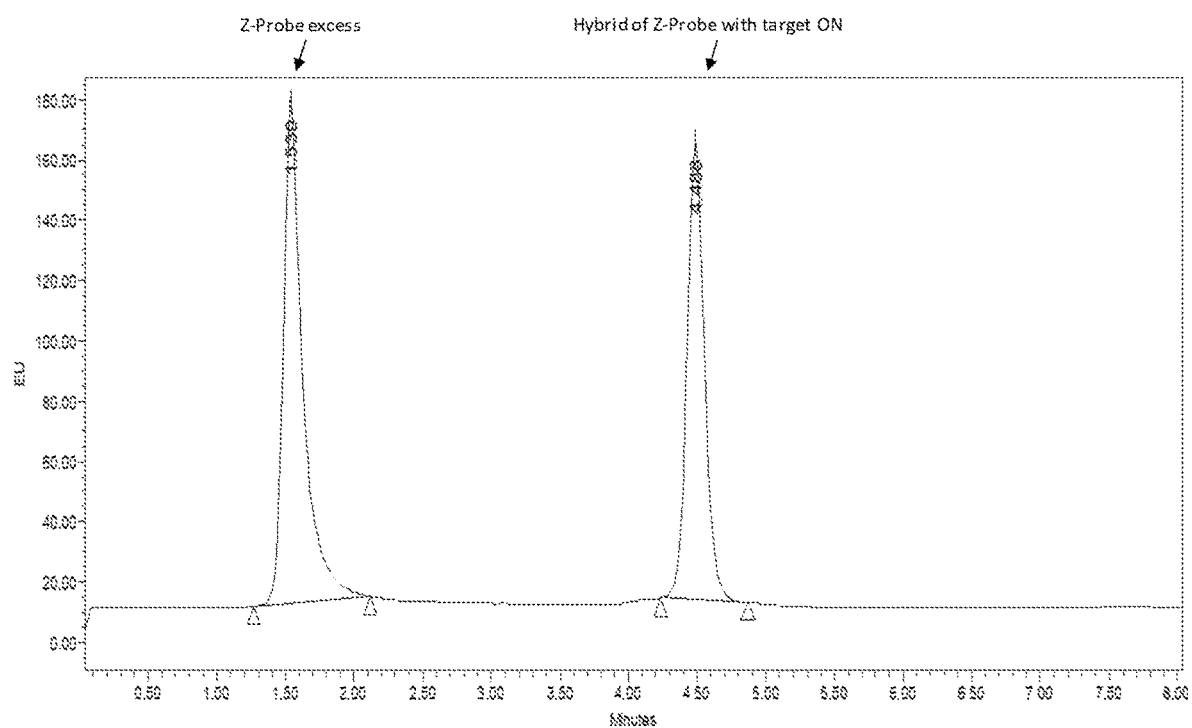
FIG. 8 shows the Ion-Exchange HPLC analysis with fluorescent detection of 19-mer synthetic 2'-O-Me RNA (Seq. 14, Table 1) annealed with excess of complementary 19-mer 2'-OMe Z-probe labeled with Cy3 on its 5' termini and comprising 6 charge modifying moiety (CMG5 from FIG. 1) on the internucleoside linkages (Seq. 15, Table 1).

The chromatography system was Waters 2695 controlled by Empower 2 software and equipped with a photodiode array (Waters, model 996) and a multiwavelength fluorescent detectors (Waters, model 2475) in a series. The separation was achieved using an anion-exchange DNAPac PA100 column (4.0×250 mm, Thermo-Dionex) protected with DNAPac PA-100 guard column (4.0×50 mm) at ambient temperature (~24° C.). Mobile phase A was Tris-HCl 25 mM, EDTA 1 mM, acetonitrile 10%, pH 7.50; mobile phase B was 500 mM NaClO$_4$, Tris-HCl 25 mM, EDTA 1 mM, acetonitrile 10%, pH 7.50. The flow rate was 1.0 mL/min. The elution was performed with a liner gradient from 10% B in A to 100% B for 8 min. The column was equilibrated at initial conditions for 5 min before each run. The Cy-3 fluorescence was detected by excitation at 554 nm and emission monitoring at 568 nm. A representative HPLC chromatogram in FIG. 8 shows an excellent separation between the peak of the unhybridized Z-Probe with retention time of 1.539 min and the peak of the duplex of the Z-Probe with the targeted ON at 4.488 min.

Figure 9:
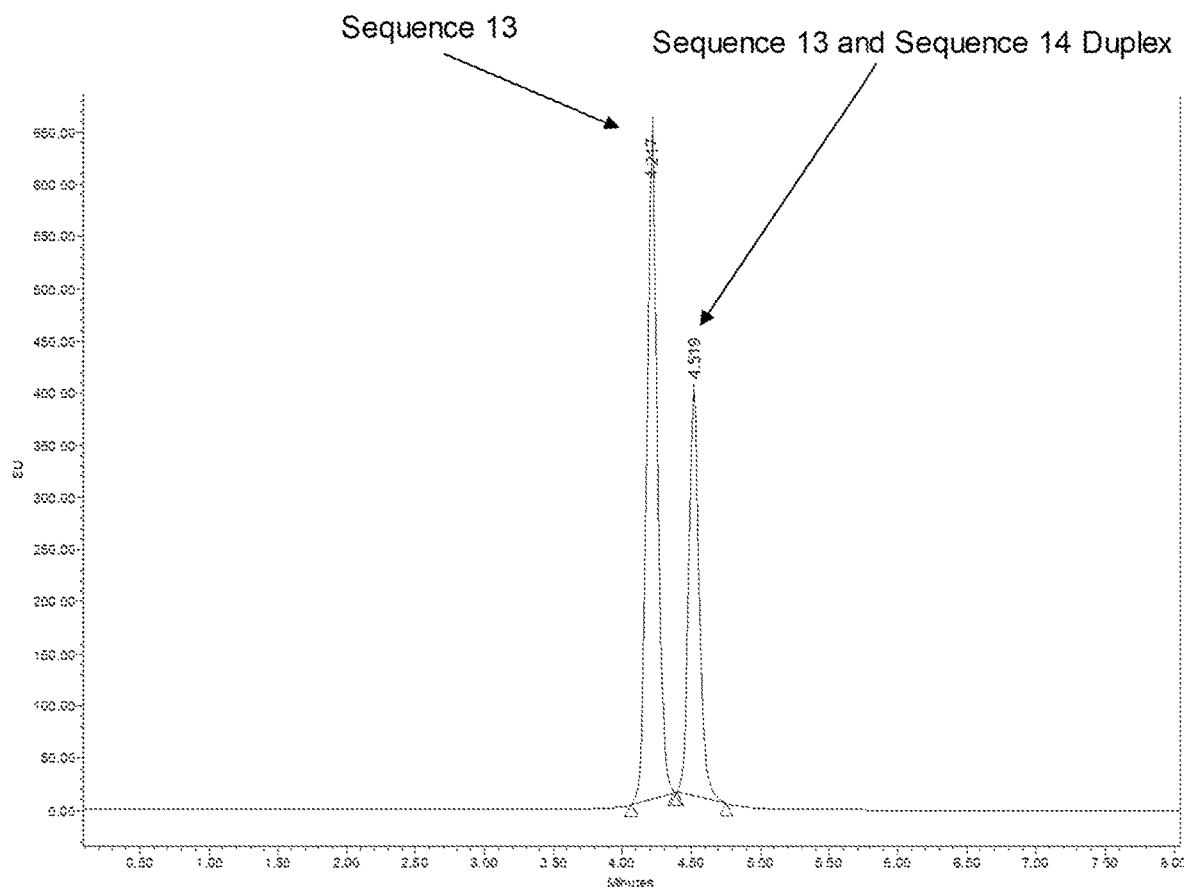
FIG. 9 shows the Ion-Exchange HPLC analysis with fluorescent detection of 19-mer synthetic 2'-OMe RNA (Seq. 14, Table 1) annealed with excess of complementary 16-mer 2'-OMe oligonucleotide labeled with Cy3 on its 5' termini (Seq. 13, Table 1).

In a control experiment, a 16-mer 2'-O-Me RNA labeled at the 5' end with Cy-3 (Seq. 13 at Table 1) was hybridized with Seq. 14 and subjected to analysis as per the conditions described above. The representative chromatogram at FIG. 9 shows lack of baseline separation of unhybridized Sequence 13 and its hybrid with Sequence 14.

Example 4

Detection of Backbone Stabilized siRNA Strands by Using Z-Probes

The purpose of this experiment is to demonstrate the detection and quantification of siRNA by using a Z-probe according to the methods of this invention. For this purpose, a siRNA was prepared by annealing Seq. 10 from Table 1 with its complementary 13-mer sequence (not shown in Table 1). A Z-probe (Seq. 8, Table 1) complimentary to the antisense strand of the siRNA (Seq. 10, Table 1) and labeled with Cy5 on its 5' end was prepared and used as per the methods of this invention.

Figure 10:
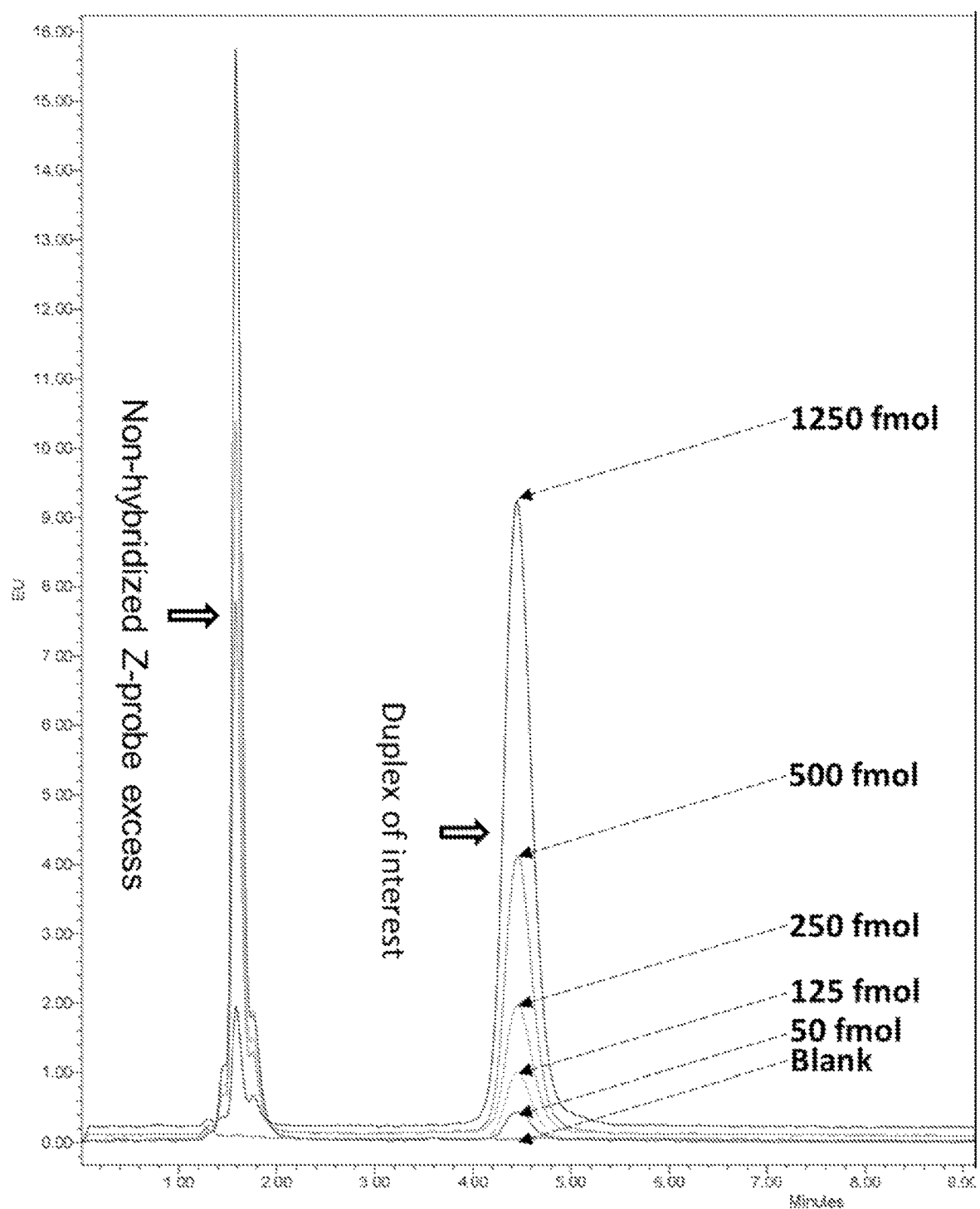
FIG. 10 shows the detection by ion-exchange HPLC of a duplex formed between a Z-probe (Seq. 8, Table 1) and its complementary strand (Seq. 10, Table 1). This duplex was formed by incubation of siRNA consisting of Seq. 10 and its complementary 13-mer RNA (0.2, 0.5, 1, 2 and 5 pmol siRNA) with 5 pmol of Z-probe. One fifth of this mixture was subject to analysis.

Various amounts (200 fmol, 500 fmol, 1 pmol, 2 pmol and 5 pmol) of siRNA were annealed with 5 pmol of the Z-probe (5 µL of 1 µM) in hybridization buffer (200 µL final volume) as described in Example 3. Fifty µL of this mixture were injected for ion-exchange HPLC analysis with fluorescence detection as described in Example 3, but with excitation at 554 and emission at 568 nm. The separation of the nonhybridized Cy5 labeled Z-probe (Seq. 8, Table 1) and its duplex with the antisense strand of the siRNA (Seq. 10, Table 1) is shown in FIG. 10.

Figure 11:
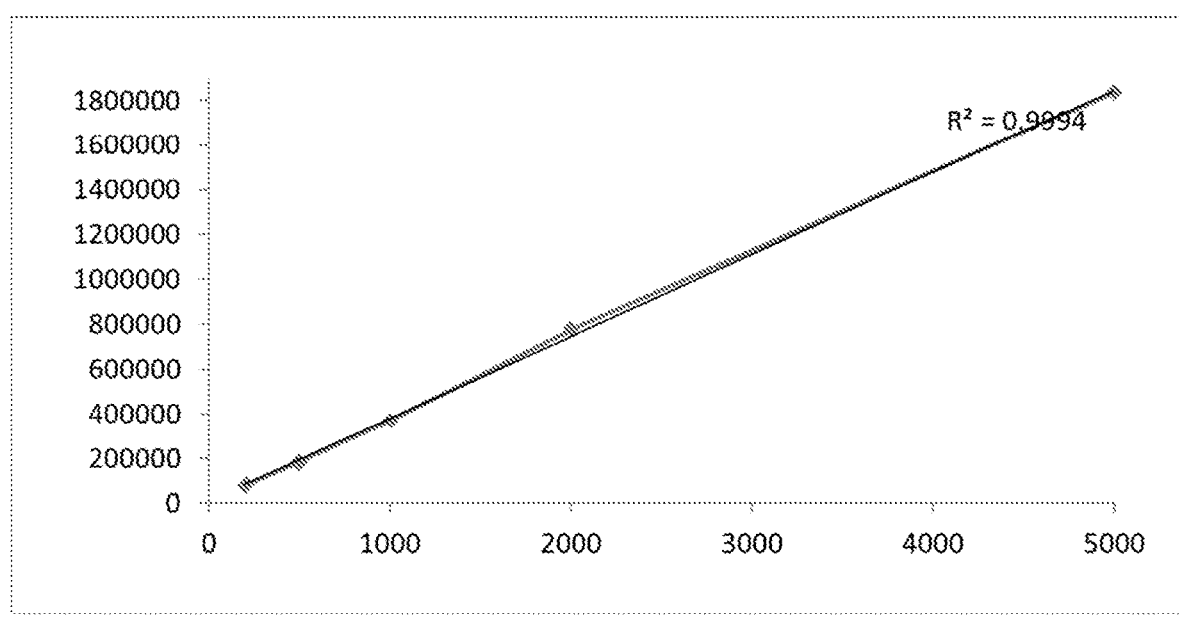
FIG. 11 shows the linearity of the calibration curve generated by analysis by ion-exchange HPLC with fluorescent detection of different amounts of duplex formed by annealing of a Z-probe (Seq. 8, Table 1) with the siRNA of interest.

The plot of the peak areas of the duplex of interest shows good linearity of the signal response between 50 and 1250 fmol per injection as shown in FIG. 11. Extrapolation of this curve to the noise/background signal in the detection area of the duplex resulted in Limit of Detection (LoD) of ~10 fmol (S/N=3) and Limit of Quantification (LoQ), ~30 fmol (S/N=10) of siRNA per injection.

Example 5

Detection of Modified siRNA in Serum by Using Z-Probe

The purpose of this experiment is to demonstrate the detection and quantification of synthetic modified siRNA in serum by using a Z-probe employing the methods of this invention. In this experiment, human serum was spiked with synthetic modified siRNA (the siRNA described in Example 4), followed by RNA extraction, annealing with a Z-probe (Seq. 8, Table 1) and analysis by HPLC as per Example 4.

Figure 12:
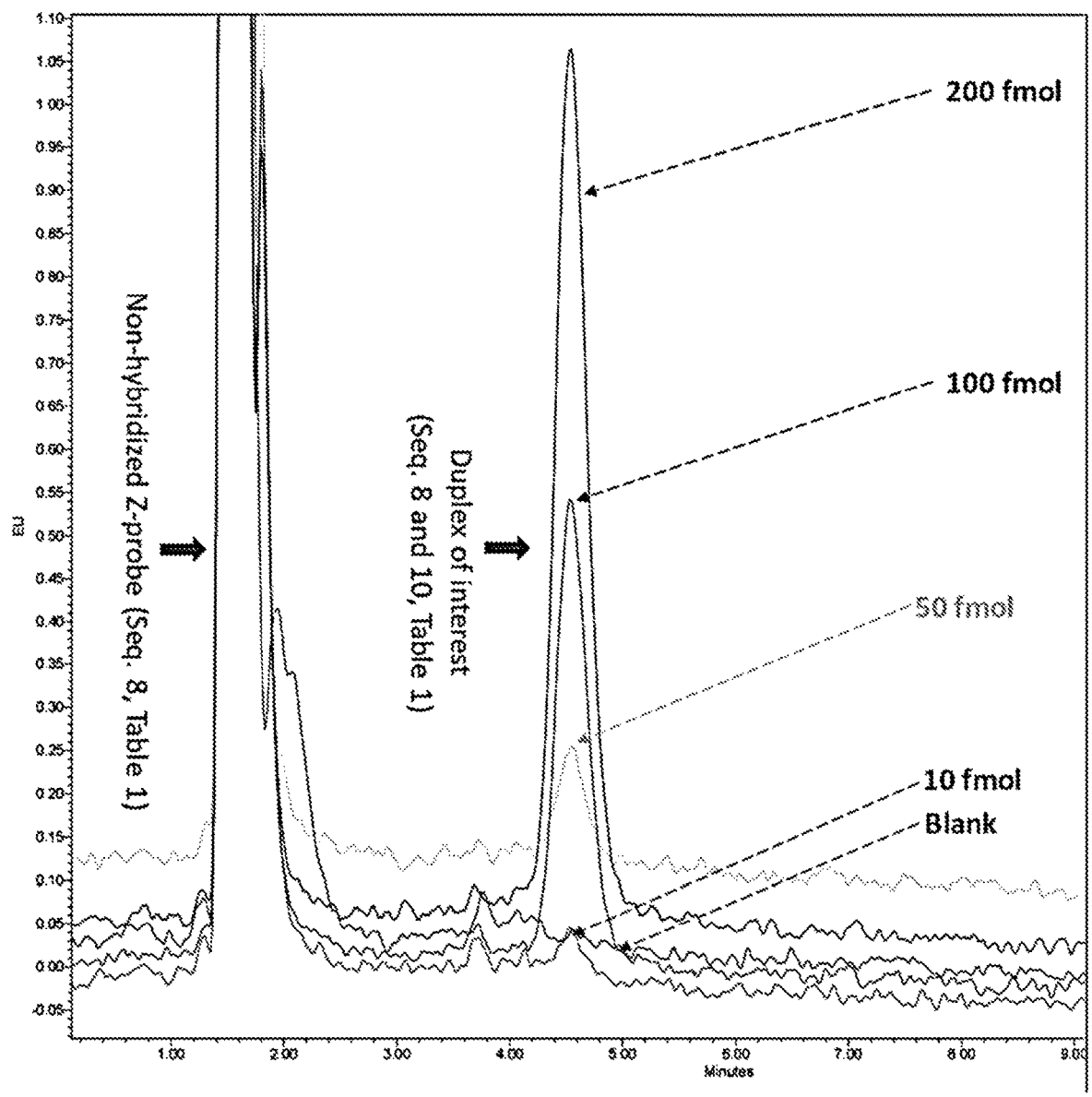
FIG. 12 shows the analysis of siRNA in serum using a Z-probe (Sequence 8) and ion-exchange HPLC with fluorescent detection for determination of the duplex formed between the Z-probe and the siRNA antisense strand according to the procedure in Example 3.

The procedure described by Godinho et al. in "Pharmacokinetic Profiling of Conjugated Therapeutic Oligonucleotides: A High-Throughput Method Based Upon Serial Blood Microsampling Coupled to Peptide Nucleic Acid Hybridization Assay", Nucleic acid therapeutics, vol. 27 (6), pages 323-34 was adapted for the extraction of siRNA from serum. Shortly, 50 µL aliquots of serum were spiked with different amounts of siRNA (100 fmol, 500 fmol, 1 pmol and 2 pmol), and then 100 µL of SDS-containing lysis solution (Epicentre) and 4 µL proteinase K (20 mg/µL) were added. After incubation at 65° C. for 20 min, additional 100 µL of lysis solution were added and SDS was precipitated with 20 µL 3M KCl. The samples were centrifuged at 15,000 g for 15 min and the supernatants were used for hybridization with Cy-5 labeled Z-probe (Seq. 8, Table 1) as per Example 3. For that purpose, 50 µL of supernatant were mixed with 50 µL of 1 µM Z-probe in HB. The mixture was annealed as per Example 3 and 50 µL were injected for HPLC analysis. Blank serum sample (without addition of RNA) was processed in parallel to establish baseline. Representative HPLC chromatograms shown in FIG. 12 demonstrate that ~60% charge-neutralization in the Z-probes is sufficient for complete separation of a large excess (up to 500×) of the Z-probe from its duplex with the analyzed oligonucleotide. The LoQ was not much different from the one in buffer (Example 4) and was ~15 fmol per injection. This example illustrates that Z-probes are highly sensitive (10-15 fmol on column) and selective diagnostic probes which can be used for the detection of small nucleic acids of interest in samples.

Example 6

Control of Z-Probes hybridization strength by modifying the ionic strength of the hybridization buffer. Detection of double stranded RNA.

The purpose of this example is to demonstrate that hybridization strength of the Z-probes with their targeted nucleic acids can be modulated (increased or decreased) by varying the ionic strength of the hybridization buffer. In examples 1 and 2 it was demonstrated that the hybridization strength of the Z-probes with their complementary nucleic acids increases with the decrease of the ionic strength of the hybridization buffer, and that this effect is proportional to the number of CMG groups in the Z-probe. In this example we show that this effect can be used to increase the efficiency of displacement of the non-targeted strand and therefore the efficiency of detection of double-stranded nucleic acid. Alternatively, the decrease of the hybridization strength in high ionic strength buffer may be beneficial for decreasing of off-target detection due to hybridization with partially miss-matched off-target sequences when targeting single stranded nucleic acids.

Synthetic 23-mer RNA (Sequence 16 in Table 1), 9 µM was hybridized with 18 µM of complementary 23-mer Z-probe (2'-O-Me) having 8 CMG5 (Sequence 17 in Table 1) in presence of 18 µM of control 23-mer 2'-O-Me ON with the same sequence as the Z-probe (Sequence 18 in Table 1) in low (0.01 M sodium phosphate pH 7) and high (0.01 sodium phosphate pH 7 plus 0.15 M sodium chloride) buffer by heating for 3 min at 90° C. and then cooling down to room temperature at a rate of 1° C./min. Separately, for control and detection purposes the hybrids of the Z-probe and the control ON with the targeted RNA were prepared by annealing of equimolar amount of Sequence 17 with Sequence 16 and Sequence 18 with Sequence 16. The annealed mixtures were analyzed by ion-exchange HPLC using the conditions, described in Example 3. The detection was done by UV at 260 nm.

Figure 13:
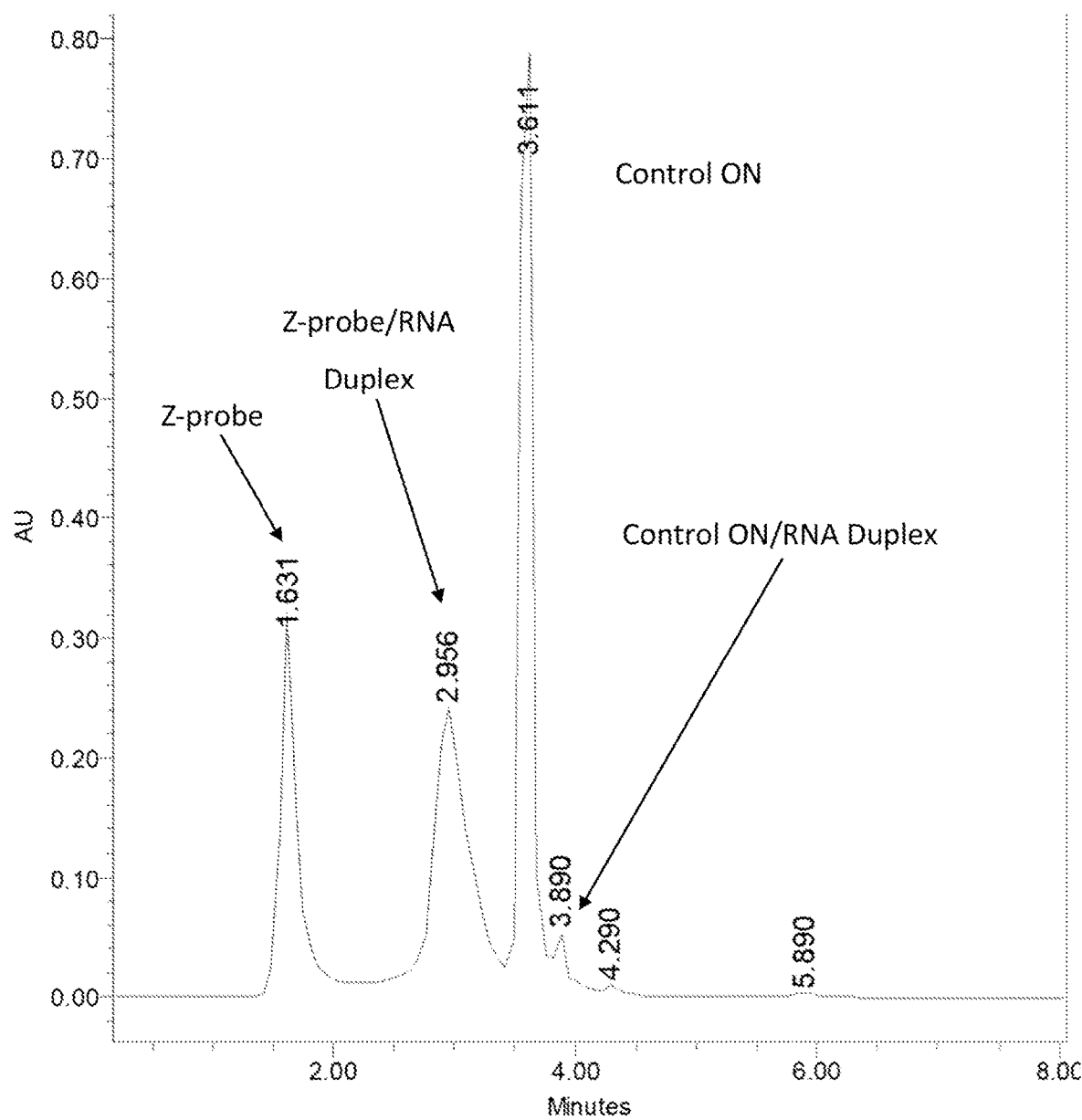
FIG. 13 shows the analysis of a mixture of a Z-Probe (Sequence 17) and a control ON (Sequence 18) annealed with complementary RNA (Sequence 16) in 2:2:1 molar ratio in a low ionic strength buffer.
Figure 14:
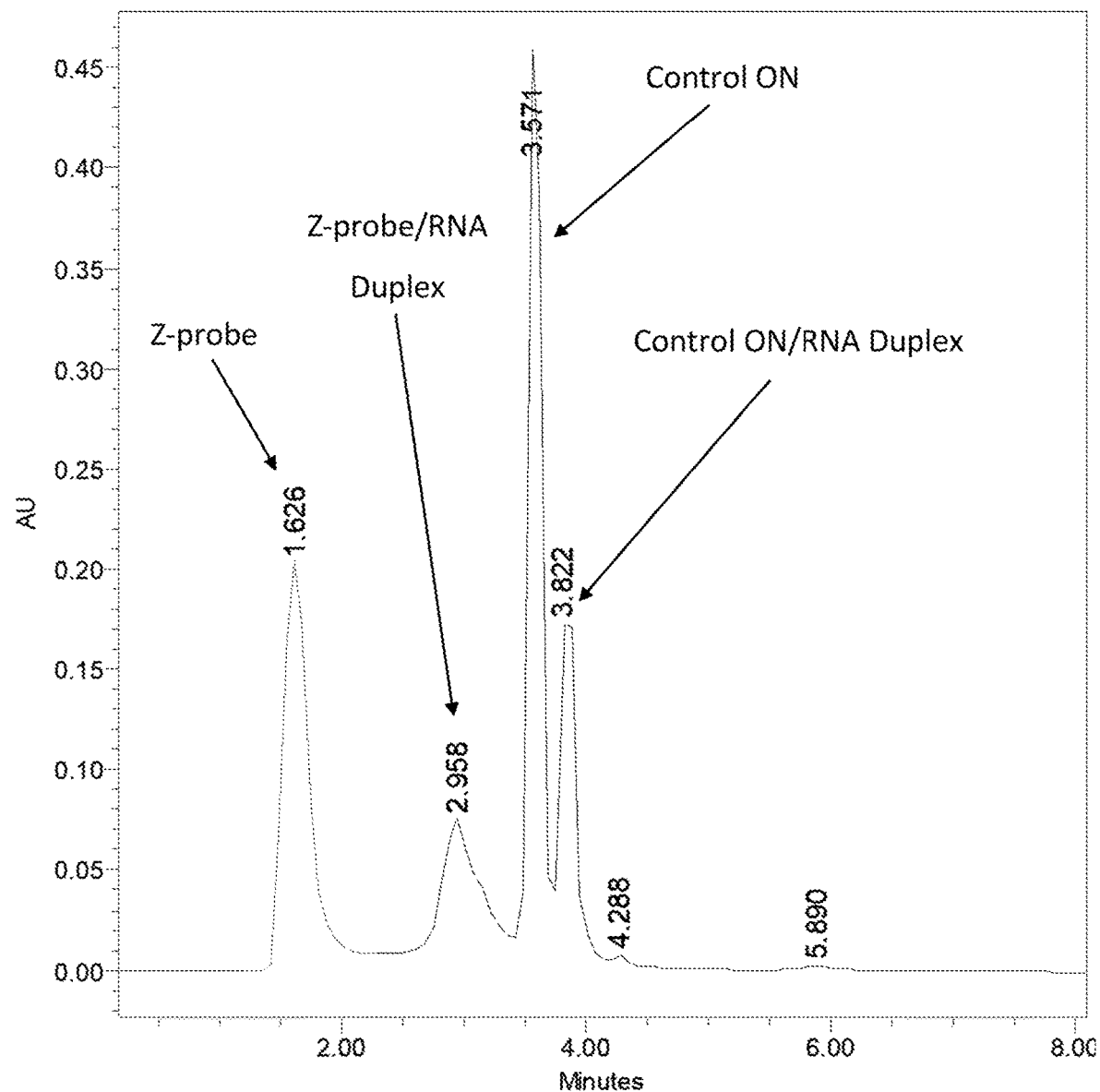
FIG. 14 shows the analysis of a mixture of a Z-Probe (Sequence 17) and a control ON (Sequence 18) annealed with complementary RNA (Sequence 16) in 2:2:1 molar ratio in a high ionic strength buffer.

The analysis of the mixture annealed at a low ionic strength buffer, shown in FIG. 13 demonstrates that the Z-probe almost completely outcompetes the Control ON for hybridization with the complementary RNA. At the same time, when the hybridization is performed in a high ionic strength buffer (analysis shown in FIG. 14) both the hybrids of the Z-probe and the control ON are present in ca. 1:1 ratio.

Example 7

Modulation of the HPLC Retention Time of a Z-Probe/Synthetic ON Duplex by Variation of Number of CMG in the Z-Probe The purpose of this example is to demonstrate modulation of retention time of duplex formed Z-Probes to the target nucleic acid of interest. For this purpose, synthetic 23-mer RNA (Seq. 9, Table 1) was annealed to 23-mer Z-Probe (Seq. 7, Table 1) containing 3 CMG (GMG5, FIG. 1) as described in example 3. Three CMG only partially neutralized backbone of Z-Probe (~45% backbone modification).

Ion-exchange HPLC analysis with fluorescence detection demonstrate shift in retention time of Seq.7/Seq.9 duplex vs analog duplex when Z-Probe contains larger number of CMGs (HPLC profiles are not shown).

Example 8

Oligonucleotides and Z-Probes Synthesis

All oligonucleotides were synthesized and de-blocked using standard phosphoroamidite chemistry on commercial synthesizers (ABI 394 and Expedite 8909 manufactured by Applied Biosystems) according to the manufacturer's protocols and using commercially available phosphoroamidites and reagents (ChemGenes Corp., Wilmington, MA and Glen Research, Inc., Sterling, VA). The purification was performed by using reversed phase cartridges or reversed phase HPLC before removal of the 5'-protecting dimethoxytrityl group. The identity was determined by electrospray mass-spectrometry and the purity was determined by analytical ion-exchange HPLC with UV detection and was above 95%. The Z-probes were synthesized and purified using the same instrumentation and methodology, except that the nucleotide units bearing CMGs were incorporated using CMG bearing phosphoroamidites, which were prepared as described below.

Synthesis, Purification and Characterization of Phosphoramidites for Introduction of CMGs in Z-Probes The methodology described in Yanachkov et al. *Org. Biomo.l Chem.* 2017 Feb. 7; 15 (6), 1363-1380 was adopted for the synthesis of 2'-O-Me phosphoroamidites used for the incorporation of CMGs (FIG. 1) in the Z-Probes. 5'-DMTr and base protected 2'-O-Me nucleosides were obtained from ChemGenes Corporation (Wilmington, MA).

General structures of synthesized 5'-Dimethoxytrityl-N-acetyl-2'-OMe-Cytidine, 3'-[(1,3-Bis(2-(dimethylamino)ethoxy)propan-2-ol)-(N,N-diisopropyl)]-phosphoramidite, 5'-Dimethoxytrityl-N-benzoyl-2'-OMe-Adenine, 3'-[(1,3-Bis(2-(dimethylamino)ethoxy)propan-2-01)-(N,N-diisopropyl)]-phosphoramidite, 5'-Dimethoxytrityl-N-isobutyryl-2'-OMe-Guanine, 3'-[(1,3-Bis(2-(dimethylamino)ethoxy)propan-2-01)-(N,N-diisopropyl)]-phosphoramidite, and 5'-Dimethoxytrityl-2'-OMe-Uridine, 3'-[(1,3-Bis(2-(dimethylamino)ethoxy)propan-2-01)-(N,N-diisopropyl)]-phosphoramidite are shown below.

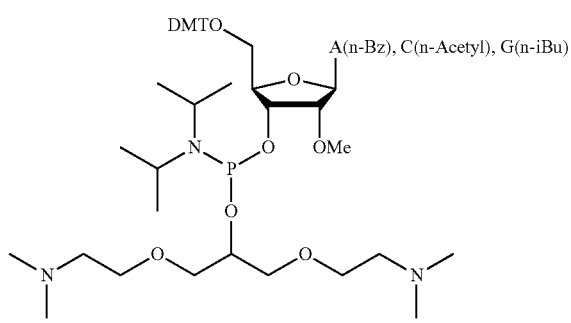

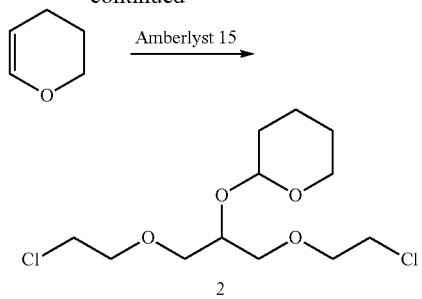

The identity and the purity of the synthesized amidites were determined by LS/MS, 1H and 31P NMR spectroscopy.

Synthesis of Charge Modifying Groups (CMGs)

The methodology for the synthesis of the CMSs necessary for the preparation of the CMG bearing phosphoroamidites was adopted from Yanachkov et al., "Self-neutralizing ONs with enhanced cellular uptake", Org. Biomol. Chem., vol. 15 (6), pages 1363-80 (2016). As an example, below is presented the synthesis of CMG6 and a CMG6 bearing phosphoroamidite.

1.1.  N,N'-di(Trifluoroacetyl)-N-methylpropane-1,3-diamine (1)

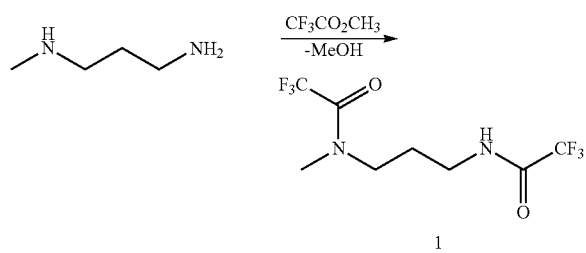

Methyl trifluoroacetate and N-methylpropane-1,3-diamine were dried over molecular sieve 3A. N-methylpropane-1,3-diamine, 0.239 mol, 21.1 g, 25.0 ml was added on stirring to methyl trifluoroacetate, 0.718 mol, 91.9 g, 72.2 ml under reflux condenser at such a rate as to maintain a gentle reflux, then mixture was refluxed for 3 h under Argon. The reaction mixture was cooled, diluted with 200 ml ethyl acetate and washed 2×250 ml 5% citric acid. The combined citric acid washings were extracted back with 150 ml ethyl acetate. The combined ethyl acetate layers were washed with 100 ml saturated brine, filtered through cotton plug and evaporated on rotary evaporator at 7 torr and 45° C. After final drying at 0.1 torr and 70° C. 63.7 g, 95.1% of N,N'-di(trifluoroacetyl)-N-methylpropane-1,3-diamine were obtained as yellowish oil. $^1$H and $^{13}$C NMR spectra reveal two isomers in 4.5:1 ratio due to hindered rotation around the CF$_3$CO—N(Me) bond. $^1$H NMR (500 MHz, CDCl$_3$), δ: major isomer, 7.62 (bs, 1H), 3.53 (t, J=6.45 Hz, 2H), 3.33 (q, J=6.33 Hz, 2H), 3.17 (m, 3H), 1.88 (m, 2H); minor isomer, 7.43 (bs, 1H), 3.47 (m, 2H), 3.40 (q, J=6.67 Hz, 2H), 3.03 (s, 3H), 1.95 (m, 2H); $^{13}$C NMR (126 MHz, CDCl$_3$) δ: 158.5-156.6 (four quartets, $^2J_{CF}$=36.9 Hz), 120-112 (four quartets, $^1J_{CF}$=287 Hz), 46.89 (q, $^4J_{CF}$=3.07 Hz), 46.38, 36.96, 36.18, 34.88 (q, $^4J_{CF}$=3.95 Hz), 34.27, 27.66, 25.54.

1.2.  2-((1,3-Bis(2-chloroethoxy)propan-2-yl)oxy)tetrahydro-2H-pyran (2)

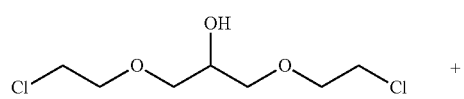

Dry Amberlist® 15, 0.1 g was added to a water-cooled mixture of 1,3-bis(2-chloroethoxy)propan-2-ol, 23 mmol, 5.00 g and 3,4-dihydro-2H-pyran, 0.115 mol, 9.68 g, 10.5 ml. The mixture was stirred at rt for 2 h. The resin was filtered and washed with 5 ml ethyl acetate. The combined filtrate and washings were diluted with ethyl acetate, 100 ml and washed with 5% sodium hydrogen carbonate solution. The aqueous layer was extracted with 50 ml ethyl acetate. The combined organic layers were washed with saturated brine and then diluted with 300 ml toluene, filtered through a cotton plug and vacuum evaporated to an oil, 9.60 g. This oil was purified on silica gel column, which was pre-treated with 20% triethylamine in petroleum ether, and equilibrated with petroleum ether. The product was eluted with a gradient from petroleum ether to petroleum ether/ethyl acetate/2-propanol 5:5:1, to obtain, after vacuum evaporation, 6.17 g, 89% of 2. $^1$H NMR (500 MHz, C$_6$D$_6$), δ: 4.82 (m, 1H), 4.00 (m, 1H), 3.88 (m, 1H), 3.56 (m, 1H), 3.49 (m, 2H), 3.41-3.26 (m, 6H), 3.19 (m, 4H), 1.76-1.55 (m, 3H), 1.37-1.24 (m, 3H); $^{13}$C NMR (126 MHz, C$_6$D$_6$) δ:f 98.24, 74.41, 71.19, 71.06, 61.85, 42.65, 30.89, 25.53, 19.44.

1.3.  2-((1,3-Bis(2-iodoethoxy)propan-2-yl)oxy)tetrahydro-2H-pyran (3)

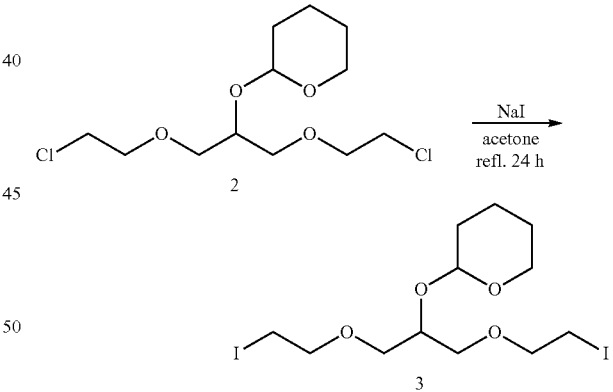

A mixture of 1,3-bis(2-chloroethoxy)propan-2-ol (2), 13.3 mmol, 4.00 g, and finely ground potassium iodide, 10 g in 10 ml acetone was stirred under reflux for 24 h. The solids were filtered and washed with 50 ml ether. The combined filtrates were evaporated under vacuum to give 6.48 g, 100% of crude 2-((1,3-bis(2-iodoethoxy)propan-2-yl)oxy)tetrahydro-2H-pyran (3) as a dark yellow oil, which was stored at −20° C. under Argon and used without further purification. $^1$H NMR (500 MHz, C$_6$D$_6$), δ: 4.84 (m, 1H), 3.99 (m, 1H), 3.88 (m, 1H), 3.54 (m, 1H), 3.46 (m, 2H), 3.40-3.26 (m, 6H), 2.82 (m, 4H), 1.77-1.52 (m, 3H), 1.38-1.24 (m, 3H); $^{13}$C NMR (126 MHz, C$_6$D$_6$) δ:f 98.24, 74.41, 71.19, 71.06, 61.85, 42.65, 30.89, 25.53, 19.44; $^{13}$C NMR (126 MHz, C$_6$D$_6$) δ: 98.22, 74.40, 71.67, 71.64, 70.87, 70.77, 61.92, 30.94, 25.56, 19.48, 3.20, 3.16.

1.4. 2,6,16,20-(tetrakis(2,2,2-trifluoroacetyl)-9,13-dioxa-2,6,16,20-tetraazahenicosan-11-ol (4)

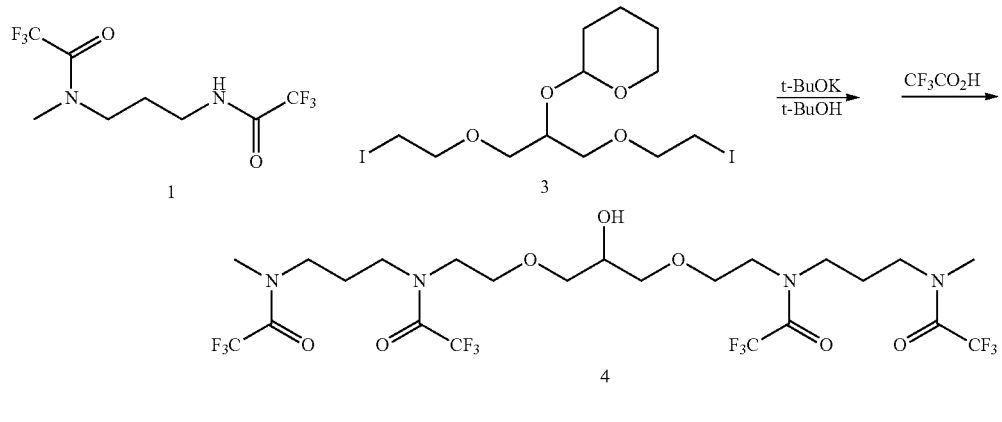

Tert-Potassium butoxide, 1M solution in t-butanol, 6.30 ml, 6.30 mmol was added dropwise on cooling (ice) and stirring to N,N'-di(trifluoroacetyl)-N-methylpropane-1,3-diamine (1), 7.56 mmol, 2.12 g under Argon and the resulted solution was concentrated under vacuum. Crude 2-((1,3-bis(2-iodoethoxy)propan-2-yl)oxy)tetrahydro-2H-pyran (3), 2.52 mmol, 1.22 g was added and the mixture was stirred under Argon at rt for 4 days. The reaction mixture was diluted with ethyl acetate, 150 ml and washed with 100 ml of 5% citric acid. The citric acid washing was extracted back with 50 ml ethyl acetate. The combined ethyl acetate extracts were washed with saturated saline, 50 ml, filtered through a cotton plug and evaporated under vacuum to give 2.74 g of oily residue. This residue was dissolved in trifluoroacetic acid, 6 ml and left at rt for 2 h. The trifluoroacetic acid was evaporated under vacuum and the residue was evaporated twice from acetonitrile. The residue was dissolved in DMSO, 5 ml and was purified by preparative HPLC in three equal injections, using XBridge C18, 5 μm, 20×250 mm column (Waters) and a gradient from 0.1% formic acid in water (A) to 0.1% formic acid in acetonitrile (B) at flow rate of 15 ml/min and UV detection at 220 nm. The gradient program (% B in A) was from 0 to 35 for 5 min, then to 70 for 35 min, then to 100 for 5 min and then isocratic at 100% B for 5 min. The fractions containing pure product were evaporated under vacuum to obtain 445 mg, 22% of 2,6,16,20-(tetrakis(2,2,2-trifluoroacetyl)-9,13-dioxa-2,6,16,20-tetraazahenicosan-11-ol (4). The $^1$H and $^{13}$C NMR spectra reveal number of isomers due to restricted rotation around the $CF_3CO-N$ bonds. $^1$H NMR (500 MHz, $C_6D_6$), δ: 3.90-3.81 (m, 1H), 3.49-3.40 (m, 2H), 3.36-3.12 (mm, 14H), 3.03-2.80 (mm, 4H), 2.62-2.43 (ms, 6H), 1.61-1.37 (mm, 4H), 0.79 (bs, 1H); $^{13}$C NMR (126 MHz, $C_6D_6$) δ: 156.9 (mq, $^2J_{CF}$=35.4 Hz), 117.3 (mq, $^1J_{CF}$=287 Hz), 73.04-68.8 (ms, $CH_2O$), 47.8-45.4 (overlapping ms and mq, $CH_2N$), 33.2-34.7 (ms, $CH_3N$), 27.1-23.8 (ms, $CH_2CH_2CH_2$); MS (ESI$^+$) m/z: observed, 704.8 (100%), 705.8 (21.4%), 706.7 (5.6%), calculated for $C_{23}H_{33}F_{12}N_4O_7$, 705.2 (100.0%), 706.2 (24.9%), 707.2 (4.4%).

1.5. Phorphoroamidite (5)

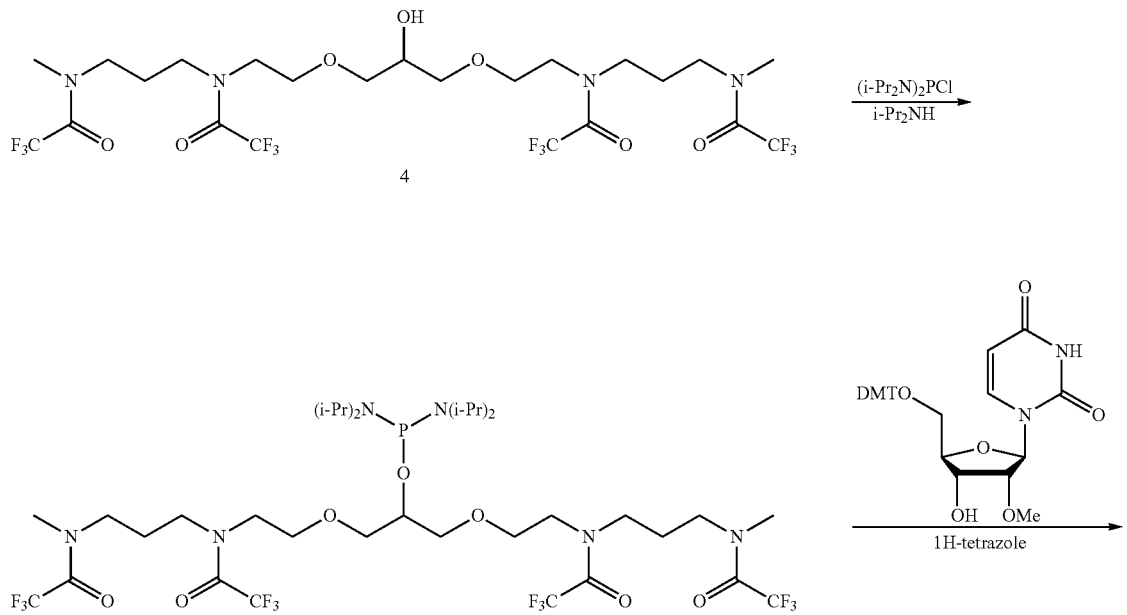

-continued

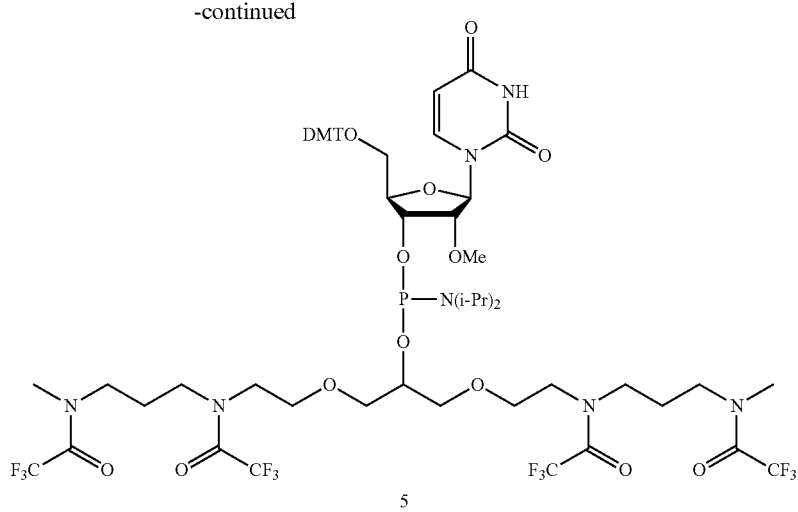

5

2,6,16,20-Tetrakis(2,2,2-trifluoroacetyl)-9,13-dioxa-2,6,16,20-tetraazahenicosan-11-ol (4) 0.362 mmol, 255 mg was dried by evaporating three times form a mixture 1:1 of dry toluene and dry acetonitrile. The residue was dissolved in dry tetrahydrofuran, 1 ml and cooled under Argon in dry ice/acetone mixture. Dry diisopropylamine, 0.742 mmol, 73.3 mg, 102 μL was added on stirring, followed by a solution of bis(diisopropylamino)-chlorophosphine, 0.398 mmol, 73.3 mg in 0.5 ml dry tetrahydrofuran. The reaction mixture was left overnight at rt. 5'-O-(4,4'-Dimethoxytrityl-2'-O-methylurydine, 0.380 mmol, 213.1 mg was dissolved in 3 ml dry N,N-dimethylformamide, concentrated under vacuum to 0.5 ml and added to the reaction mixture on stirring, followed by 1 mL of 0.4 M solution of tetrazole in acetonitrile. The mixture was left for 24 h at rt and under Argon, then diluted with dichloromethane, 50 ml, washed with 100 ml of ice-cold 5% solution of sodium hydrogen carbonate, filtered through a cotton plug and concentrated under vacuum. The product was purified by flash chromatography on a 40 g spherical silica gel cartridge (30 μm), which was pre-equilibrated with 10% triethylamine in hexanes and then with 0.5% triethylamine in hexanes. The cartridge was eluted with a 30 min gradient from 0.5% triethylamine in hexanes to 0.5% triethylamine in ethyl acetate and then isocratically for 30 min with 0.5% triethylamine in ethyl acetate at a flow rate of 15 mL/min. The fractions containing pure product were combined and evaporated under vacuum. The residue was dried by evaporation from anhydrous acetonitrile (2×) and from anhydrous toluene (2×) to give 291 mg, 58% of phosphoroamidite 5 as a mixture of two diastereomers. Purity by reversed phase HPLC, above 95%. Purity by $^{31}$P NMR—no extraneous peaks observed. $^1$H NMR (500 MHz, $C_6D_6$), conforms to structure, see appendix for spectra); $^{13}$C NMR (126 MHz, $C_6D_6$) conforms to structure, see appendix for spectra); $^{31}$P NMR (203 MHz, $C_6D_6$), 151.0 (ms), 149.7 (ms); MS (ESI$^-$) m/z: observed, 1392.2 (100%), 1393.1 (55.0%), 1394.0 (20.5%), 1395.0 (5.3%); calculated for $C_{60}H_{75}F_{12}N_7O_{15}P^-$, 1392.5 (100.0%), 1393.5 (64.9%), 1394.5 (20.7%), 1395.5 (6.4%).

What is claimed is:

1. A method for detection of one or more target nucleic acids in a sample, the method comprising:

contacting the sample with a charge-modified oligonucleotide probe, wherein the charge-modified oligonucleotide probe comprises an oligonucleotide sequence that is complimentary, or partially complimentary, to the one or more target nucleic acids, and wherein the charge-modified oligonucleotide probe has the structure (I)

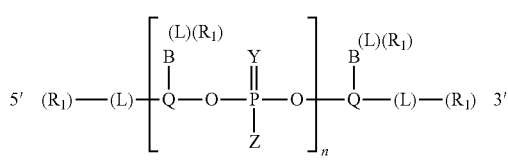

wherein
each B is independently selected from a nucleobase moiety;
each Q is independently selected from a nucleoside sugar;
each Y is independently selected from a sulfur or oxygen atom;
n is a number from 1 to 250;
each L is, independently for each occurrence, a

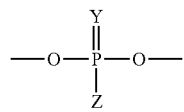

group, a linker selected from —O— or —S—; alkylenes, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, divalent ring systems; or L is not present, in which case L is a covalent bond;

each $R_1$ is, independently for each occurrence, a reporter group, or a group with high specific affinity, or a hydrogen atom;

each Z is independently selected from the group consisting of OH, SH, or a group with Structure (II):

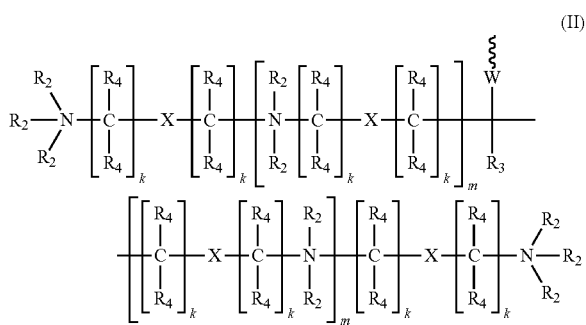

wherein:
at least one occurrence of Z is selected to be a group according to Structure II;
W is a linker selected from —O— or —S—; $C_{1-10}$ alkylenes, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, divalent ring systems; or W is not present, in which case W is a covalent bond;

each X is independently selected to be an oxygen or a sulfur atom;

each $R_2$ is independently selected from a group consisting of H, methyl, ethyl, propyl, isopropyl, methoxy, ethoxy, isopropyloxy, straight, branched, or substituted $C_{1-6}$ alkyl, $C_{2-6}$ alkene, substituted $C_{2-6}$ alkene, straight or branched $C_{1-6}$ alkoxy, or two $R_2$ together with the nitrogen atom to which they are both attached form an 5- to 7-membered single nitrogen heterocyclic ring, or 5- to 7-member heterocyclic ring having up to two additional ring heteroatoms selected from the group consisting of O, S, and N, and wherein the 5- to 7-membered heterocyclic ring may be unsubstituted or substituted with up to three substituents selected from the group consisting of halo, $C_{1-4}$ alkyl, and $C_{1-4}$ alkoxy, or is not present, in which case $R_2$ is an electron pair;

$R_3$ is selected from a group consisting of H, methyl, ethyl, propyl, isopropyl, 1,1-dimethyethyl, methoxy, ethoxy, isopropyloxy, tret-butyloxy, $C_{1-6}$ straight or branched alkyl, substituted $C_{1-6}$ straight or branched alkyl, $C_{2-6}$ alkene, and substituted $C_{2-6}$ alkene;

each $R_4$ is independently selected from a group consisting of H, methyl, ethyl, propyl, isopropyl, methoxy, ethoxy, isopropyloxy, straight, branched, or substituted $C_{1-6}$ alkyl, $C_{2-6}$ alkene, substituted $C_{2-6}$ alkene, straight or branched $C_{1-6}$ alkoxy, or two $R_4$ together with the carbon atom to which they are both attached form an 3- to 7-membered alicyclic ring, or 5- to 7-member heterocyclic ring having up to two ring heteroatoms selected from the group consisting of O, S, and N, and wherein the alicyclic or heterocyclic ring may be unsubstituted or substituted with up to three substituents selected from the group consisting of halo, $C_{1-4}$ alkyl, and $C_{1-4}$ alkoxy;

each k is, independently for each occurrence, selected from 2, 3, 4 or 5;

each m is, independently or each occurrence, selected from 0, 1, 2, 3, 4 or 5.

2. The method according to claim 1, wherein the group with Structure (II) is selected to be a group having the Structure IIA:

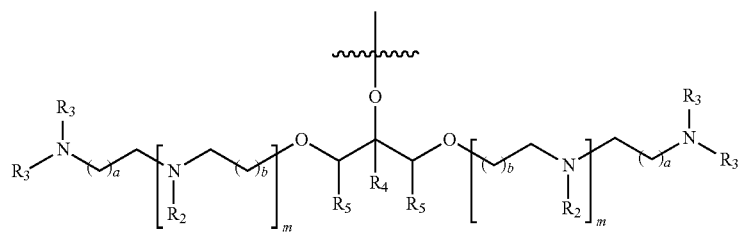

IIA wherein:
each $R_2$ is independently selected from a group consisting of H, $C_{1-6}$ alkyl, substituted $C_{1-6}$ alkyl, $C_{2-6}$ alkene, and substituted $C_{2-6}$ alkene;
each $R_3$ is independently selected from a group consisting of H, $C_{1-6}$ alkyl, substituted $C_{1-6}$ alkyl, $C_{2-6}$ alkene, and substituted $C_{2-6}$ alkene;
alternatively, two adjacent $R_3$, together with the nitrogen to which they are attached, form a 5- to 7-membered heterocyclic ring having up to two additional ring heteroatoms selected from the group consisting of O, S, and N, and wherein the 5- to 7-membered heterocyclic ring may be unsubstituted or substituted with up to three substituents selected from the group consisting of halo, alkyl, $C_{1-4}$ alkyl, and $C_{1-4}$ alkoxy;

$R_4$ is selected from the group consisting of H, $C_{1-6}$ alkyl, substituted $C_{1-6}$ alkyl;
each $R_5$ is independently selected from the group consisting of H, $C_{1-6}$ alkyl or substituted $C_{1-6}$ alkyl;
each a is independently selected from 1, 2 and 3;
each b is independently selected from 1, 2 and 3; and
each m is independently selected from 0, 1, 2, 3, 4 or 5.

3. The method according to claim 1, wherein the charge-modified oligonucleotide probe of Structure (I) has the structure (IA):

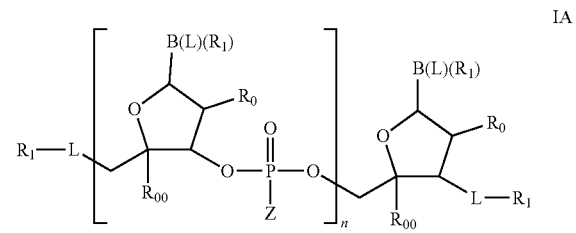

IA wherein:
each B is independently selected from a nucleobase;
n is a number from 1 to 250;
L is, independently for each occurrence, a

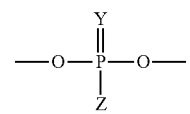

group, a linker selected from —O— or —S—; alkylenes, which may be unsubstituted or substituted with 1 to 3 substituents selected from halo, hydroxy, lower alkoxy, amino, lower alkyl amino, nitro, cyano, perfluoro alkyl, and perfluoro alkoxy; linearly connected carbon and hetero atoms, wherein the heteroatom is selected from O, S and NH, divalent ring systems; or L is not present, in which case L is a covalent bond;

each $R_0$ is independently selected from H, OH, or O-$C_{1-3}$ alkyl, substituted O-$C_{1-3}$ alkyl, O-$CH_2CH_2OCH_3$, F, or together with $R_{00}$ is a divalent moiety that forms a bridge between C2' and C4' such as —$OCH_2$-, or $OCH_2CH_2$—;

each $R_{00}$ is either, together with $R_0$ a divalent moiety that forms a bridge between C2' and C4' such as —OCH$_2$—, or OCH$_2$CH$_2$—, or is a H;

each $R_1$ is independently selected from a reporter group, or a group with high specific affinity, or a hydrogen atom;

each Z is independently selected from the group consisting of OH, SH, or a group with Structure II or Structure IIA, wherein at least one Z is selected to be a group with Structure II or IIA.

4. The method according to claim 1, wherein the reporter group is selected from the group consisting of fluorescent dyes, fluorescent quenchers, a dye that absorbs light in the visible, or near-visible infrared or ultraviolet spectrum, or a chemical moiety that contains one or more radioactive isotopes, such as, $^3$H, $^{31}$P, $^{14}$C, or $^3$H, $^{35}$S, $^{131}$I, $^{111}$In or $^{99m}$Tc, or one or more stable isotopes, such as $^2$H, $^{18}$O, $^{13}$C, $^{15}$N, or a moiety with high specific binding affinity to another moiety, such as biotin, which has high specific affinity to avidin, or an antigen with a high specific binding to an antibody.

5. The method according to claim 2, wherein one or more H, C, O, S, P and N atoms in the structure of the charge modifying oligonucleotide probe are replaced with their radioactive isotopes, such as $^3$H, $^{14}$C, $^{31}$P, $^{35}$S, or are replaced with their heavier stable isotopes, such as $^2$H, $^{18}$O, $^{13}$C, or $^{15}$N.

6. The method according to claim 1, in which the target nucleic acid is a naturally occurring, artificially expressed, or synthetic molecule comprising two or more and up to one thousand nucleosides or modified nucleosides or nucleoside analogs or nucleoside mimics covalently linked through a phosphate group, or phosphate group analog, or phosphate group mimic, or through any other divalent chemical moiety, and which small nucleic acid includes the duplex or triplex formed by H-bonding, base pairing, and in particular Watson-Crick type base pairing between two or more single stranded small nucleic acids, and which may include DNA, RNA, DNA oligonucleotides (ON), RNA oligonucleotides, such as single, or double stranded RNA, microRNA (miRNA, miR, both mature or pre-miRNA and their guide and passenger strands), transport RNA (tRNA) messenger RNA (mRNA), guiding RNA (gRNA), tracer RNA, tracrRNA, snRNA, Piwi-interacting RNA (piRNA), pathogens generated DNA or RNA, such as viral RNA or DNA, small interfering RNA (siRNA) or any of its strands, natural or synthetic ONs, modified ONs, which modified ONs may be 2'-modified nucleic acids, such as 2'-O-alkyl RNA, 2'-fluoro-DNA, arabino nucleic acid (ANA), 2'-fluoro-ANA, peptide nucleic acids (PNA), morpholino oligonucleotides (PMO), locked nucleic acids (LNA), bridged nucleic acids, bicyclic, or tricyclic nucleic acids, any oligotherpeutics, their conjugates or formulations, and any modified ONs which can contain simultaneously different types of modifications, i.e. being chimeric in nature, and may contain monomers of different types and may be covalently connected to other chemical moieties.

7. The method according to claim 1, in which the sample is an organism, a mammal, a cell, a prokaryote, an eukaryote, in vitro system that also includes tissue, blood, plasma, urine, or any bodily fluid, biopsy, cell culture, oligonucleotide-based drug formulation, an active pharmaceutical ingredients (API), or a vaccine.

8. The method according to claim 1, in which the hybrid of the charge-modified oligonucleotide probe with the target nucleic acid or a strand of the target nucleic acid is subjected to analysis using chromatography, high performance liquid chromatography, ion-exchange chromatography, ion-exchange high performance liquid chromatography, normal or reversed phase or hydrophilic interaction liquid chromatography, or hydrophobic interaction liquid chromatography, affinity chromatography, gel-permeation or gel-filtration chromatography, gel-electrophoresis or capillary gel electrophoresis.

9. The method according to claim 1, in which the hybrid of the charge-modified oligonucleotide probe with the target nucleic acid or a strand of the target nucleic acid is detected and quantified using fluorescent spectroscopy, visible, ultraviolet or near-visible infrared spectroscopy, luminescence, radioactivity detector or scintillation counter, mass spectrometry, including high resolution mass spectrometry, time of flight, quadrupole, ion-trap or orbitrap based mass spectrometry.

* * * * *